US008563264B2

(12) United States Patent
Halverson et al.

(10) Patent No.: US 8,563,264 B2
(45) Date of Patent: *Oct. 22, 2013

(54) SAMPLE PREPARATION FOR ENVIRONMENTAL SAMPLING

(75) Inventors: Kurt J. Halverson, Lake Elmo, MN (US); Stephen C. P. Joseph, Woodbury, MN (US); Raj Rajagopal, Woodbury, MN (US); Matthew D. Reier, St. Paul, MN (US); David J. Velasquez, Cannon Falls, MN (US); Cynthia D. Zook, Husdon, WI (US); Sailaja Chandrapati, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 565 days.

This patent is subject to a terminal disclaimer.

(21) Appl. No.: 12/743,245

(22) PCT Filed: Nov. 19, 2008

(86) PCT No.: PCT/US2008/084015
§ 371 (c)(1),
(2), (4) Date: May 17, 2010

(87) PCT Pub. No.: WO2009/067503
PCT Pub. Date: May 28, 2009

(65) Prior Publication Data
US 2010/0285520 A1    Nov. 11, 2010

Related U.S. Application Data

(60) Provisional application No. 60/989,332, filed on Nov. 20, 2007.

(51) Int. Cl.
*C12Q 1/24* (2006.01)
(52) U.S. Cl.
USPC ............................... 435/30; 435/309.1; 604/1

(58) Field of Classification Search
USPC .............. 435/30, 309.1; 600/572; 604/1, 416; 206/229
See application file for complete search history.

(56) References Cited

U.S. PATENT DOCUMENTS 3,163,160 A * 12/1964 Cohen .......................... 600/572
3,367,191 A    2/1968 Richard
(Continued)

FOREIGN PATENT DOCUMENTS

BE    849898    6/1977
EP    0175326   3/1986
(Continued)

OTHER PUBLICATIONS

Andrews, W. H, et al., "Food Sampling and Preparation of Sample Homogenate," Bacteriological Analytical manual Online, U.S. Food and Drug Admin., Center for Food Safety & Applied Nutrition,[Retrieved from the internet Apr. 7, 2006] pp. 1-10, http://www.cfsan.fda.gov/~ebam/bam-1.html.

(Continued)

*Primary Examiner* — Michael Hobbs
(74) *Attorney, Agent, or Firm* — Nicole J. Einerson

(57) ABSTRACT

A system and method for preparing samples to test an environmental surface for an analyte of interest. The system can include a deformable self-supporting receptacle comprising a reservoir, and a loaded substrate positioned in the reservoir of the deformable self-supporting receptacle. The loaded substrate can include a substrate and a source collected from the surface. The method can include combining the loaded substrate and a diluent in the reservoir, and agitating the loaded substrate and the diluent to form a liquid composition comprising the source and the diluent.

20 Claims, 8 Drawing Sheets

(56) References Cited

U.S. PATENT DOCUMENTS

| | | |
|---|---|---|
| 3,449,081 A | 6/1969 | Hughes |
| 3,601,317 A | 8/1971 | Genantonio |
| 3,748,905 A | 7/1973 | Fletcher et al. |
| 3,784,039 A | 1/1974 | Marco |
| 3,819,158 A | 6/1974 | Sharpe et al. |
| 4,121,306 A | 10/1978 | Bringman |
| 4,427,406 A | 1/1984 | Nielsen |
| 4,937,194 A | 6/1990 | Pattillo et al. |
| 4,984,715 A | 1/1991 | Green |
| 5,100,801 A | 3/1992 | Ward, Jr. et al. |
| 5,119,830 A | 6/1992 | Davis |
| 5,186,897 A | 2/1993 | Eason et al. |
| 5,230,865 A | 7/1993 | Hargett |
| 5,291,779 A | 3/1994 | Govoni |
| 5,341,693 A | 8/1994 | Banu |
| 5,350,080 A | 9/1994 | Brown et al. |
| 5,385,251 A | 1/1995 | Dunn |
| 5,403,551 A | 4/1995 | Galloway et al. |
| 5,403,745 A | 4/1995 | Ollington |
| 5,543,115 A | 8/1996 | Karakawa |
| 5,569,225 A | 10/1996 | Fleury |
| 5,617,972 A | 4/1997 | Morano et al. |
| 5,728,542 A | 3/1998 | Charm et al. |
| 5,728,587 A | 3/1998 | Kang |
| 5,806,711 A | 9/1998 | Morano et al. |
| 5,833,860 A | 11/1998 | Kopaciewicz et al. |
| 5,849,505 A | 12/1998 | Guirguis |
| 5,869,003 A * | 2/1999 | Nason ............ 422/411 |
| 6,021,681 A | 2/2000 | Jezek |
| 6,107,085 A * | 8/2000 | Coughlin et al. ......... 435/299.1 |
| 6,168,758 B1 | 1/2001 | Forsberg |
| 6,180,335 B1 | 1/2001 | Wilkins et al. |
| 6,187,209 B1 | 2/2001 | Shurtliff |
| 6,221,655 B1 | 4/2001 | Fung et al. |
| 6,273,600 B1 | 8/2001 | Sharpe |
| 6,303,363 B1 | 10/2001 | Ward |
| 6,338,569 B1 | 1/2002 | McGill |
| 6,458,067 B1 | 10/2002 | Dorin |
| 6,461,853 B1 | 10/2002 | Zhu |
| 6,471,069 B2 | 10/2002 | Lin |
| 6,516,953 B1 * | 2/2003 | DiCesare et al. ............. 210/516 |
| 6,536,687 B1 | 3/2003 | Navis et al. |
| 6,541,262 B1 | 4/2003 | Baugh |
| 6,576,193 B1 | 6/2003 | Cui et al. |
| 6,588,681 B2 | 7/2003 | Rothrum et al. |
| 6,595,441 B2 | 7/2003 | Navis et al. |
| 6,599,420 B2 | 7/2003 | Sugiyama et al. |
| 6,669,908 B2 | 12/2003 | Weyker et al. |
| 6,746,601 B2 | 6/2004 | Dorin |
| 6,789,945 B2 | 9/2004 | Mobs et al. |
| 6,820,824 B1 | 11/2004 | Joseph et al. |
| 6,854,875 B2 | 2/2005 | McGill |
| 6,955,099 B2 | 10/2005 | Goodin |
| 7,022,289 B1 | 4/2006 | Schlein et al. |
| 7,100,461 B2 | 9/2006 | Bradley et al. |
| 7,108,662 B2 | 9/2006 | Miller et al. |
| D532,253 S | 11/2006 | White |
| 7,147,365 B2 | 12/2006 | McGill |
| 7,168,845 B2 | 1/2007 | McGill |
| 7,188,785 B2 | 3/2007 | Joseph et al. |
| 7,211,225 B2 | 5/2007 | Ferguson et al. |
| 7,223,364 B1 | 5/2007 | Johnston et al. |
| 7,309,156 B2 | 12/2007 | McGill |
| 7,374,111 B2 | 5/2008 | Joseph et al. |
| 7,555,965 B1 | 7/2009 | Mayeaux |
| 2001/0031491 A1 | 10/2001 | Curtis |
| 2002/0000403 A1 | 1/2002 | Tanaka |
| 2002/0005747 A1 | 1/2002 | Takata |
| 2002/0015355 A1 | 2/2002 | Sanpei et al. |
| 2002/0042145 A1 | 4/2002 | Forsberg |
| 2002/0078766 A1 | 6/2002 | Diaz |
| 2002/0085957 A1 | 7/2002 | Moore |
| 2002/0094548 A1 | 7/2002 | Feistel |
| 2002/0127307 A1 | 9/2002 | McGill |
| 2002/0127630 A1 | 9/2002 | DiGuiseppi et al. |
| 2004/0014237 A1 | 1/2004 | Sugiyama |
| 2004/0015786 A1 | 1/2004 | Pugliese |
| 2004/0038425 A1 | 2/2004 | Ferguson |
| 2004/0072367 A1 | 4/2004 | Ding |
| 2004/0114457 A1 | 6/2004 | McGill |
| 2004/0140373 A1 | 7/2004 | Joseph et al. |
| 2004/0164182 A1 | 8/2004 | Joseph et al. |
| 2004/0237674 A1 | 12/2004 | Wu et al. |
| 2004/0256484 A1 | 12/2004 | Joseph et al. |
| 2004/0256485 A1 | 12/2004 | Joseph et al. |
| 2005/0023182 A1 | 2/2005 | Shah |
| 2005/0112024 A1 | 5/2005 | Guo et al. |
| 2005/0132775 A1 | 6/2005 | Lagharn, Jr. et al. |
| 2005/0244943 A1 | 11/2005 | Ladisch et al. |
| 2006/0039742 A1 * | 2/2006 | Cable et al. ................. 401/134 |
| 2006/0073538 A1 | 4/2006 | Konrad |
| 2006/0102550 A1 | 5/2006 | Joseph et al. |
| 2006/0151630 A1 | 7/2006 | Joseph et al. |
| 2006/0240458 A1 | 10/2006 | Steichen et al. |
| 2006/0275798 A1 | 12/2006 | Steichen et al. |
| 2007/0084736 A1 | 4/2007 | Igota et al. |
| 2007/0269341 A1 * | 11/2007 | Halverson et al. ............. 422/58 |
| 2007/0297698 A1 | 12/2007 | Berich |
| 2008/0054087 A1 | 3/2008 | Joseph et al. |
| 2008/0268446 A1 | 10/2008 | Steichen et al. |
| 2009/0193880 A1 | 8/2009 | Halverson et al. |

FOREIGN PATENT DOCUMENTS

| | | |
|---|---|---|
| EP | 0471947 | 2/1992 |
| EP | 1005909 | 6/2000 |
| GB | 2298272 | 8/1996 |
| JP | 61-73054 | 4/1986 |
| JP | 7-223651 | 8/1995 |
| JP | 2004-501761 | 1/2004 |
| WO | WO 86/00704 | 1/1986 |
| WO | WO 94/14068 | 6/1994 |
| WO | WO 98/07828 | 2/1998 |
| WO | WO 98/32534 | 7/1998 |
| WO | WO 98/32539 | 7/1998 |
| WO | WO 00/15328 | 3/2000 |
| WO | WO 00/42419 | 7/2000 |
| WO | WO 02/06791 | 1/2002 |
| WO | WO 03/092573 | 11/2003 |
| WO | WO 2004/031734 | 4/2004 |
| WO | WO 2004/037433 | 5/2004 |
| WO | WO 2004/060574 | 7/2004 |
| WO | WO 2004/060575 | 7/2004 |
| WO | WO 2004/094072 | 11/2004 |
| WO | WO 2004/105949 | 12/2004 |
| WO | WO 2006/037140 | 4/2006 |
| WO | WO 2006/107843 | 10/2006 |
| WO | WO 2007/016691 | 2/2007 |
| WO | WO 2007/062263 | 5/2007 |
| WO | WO 2007/079143 | 7/2007 |
| WO | WO 2007/079188 | 7/2007 |
| WO | WO 2007/137257 | 11/2007 |
| WO | WO 2009/067498 | 5/2009 |
| WO | WO 2009/067513 | 5/2009 |
| WO | WO 2009/067518 | 5/2009 |
| WO | WO 2010/080223 | 7/2010 |

OTHER PUBLICATIONS

Andrews, W.H., et al., "Usefullness of the Stomacher in a Microbiological Regulatory Laboratory," Applied and Environmental Microbiology, Jan. 1978, vol. 35, No. 1, pp. 89-93.

Fung, D.Y.C. et al., "The Pulsifier: A New Instrument for Preparing Food Suspensions for Microbiological Analysis," Journal of Rapid Methods and Automation Microbiology 6, Jun. 20, 1997, pp. 43-49.

Ingham, Steven C. et al., " Manual Shaking as an Alternative to Mechanical Stomaching in Preparing Ground Meats for Microbiological analysis," Food Protection Trends, Apr. 2004, vol. 24 No. 4, pp. 253-256.

Sharpe, A.N. et al., "Stomaching : A New Concept in Bactheriological Sample Preparation," Applied Microbiology, Aug. 1972, vol. 24, No. 2, pp. 175-178.

(56) References Cited

OTHER PUBLICATIONS

Wu, Vivian, C.H., et al., "Comparison of the Pulsifier and the Stomacher for Recovering Microorganisms in Vegetables," Journal of Rapid Methods and Automation Microbiology 11, Sep. 22, 2003, pp. 145-152, Food & Nutrition Press, Inc., Trumbull, USA.

Sharpe, et al. Ultrasound and Vortex Stirring as Bacteriological Sampling Methods for Foods, Fournal of Applied Bacteriology, 33 (1970), p. 351-357.

International Search Report PCT/US2008/084015, Feb. 24, 2009, 4 pgs.

* cited by examiner

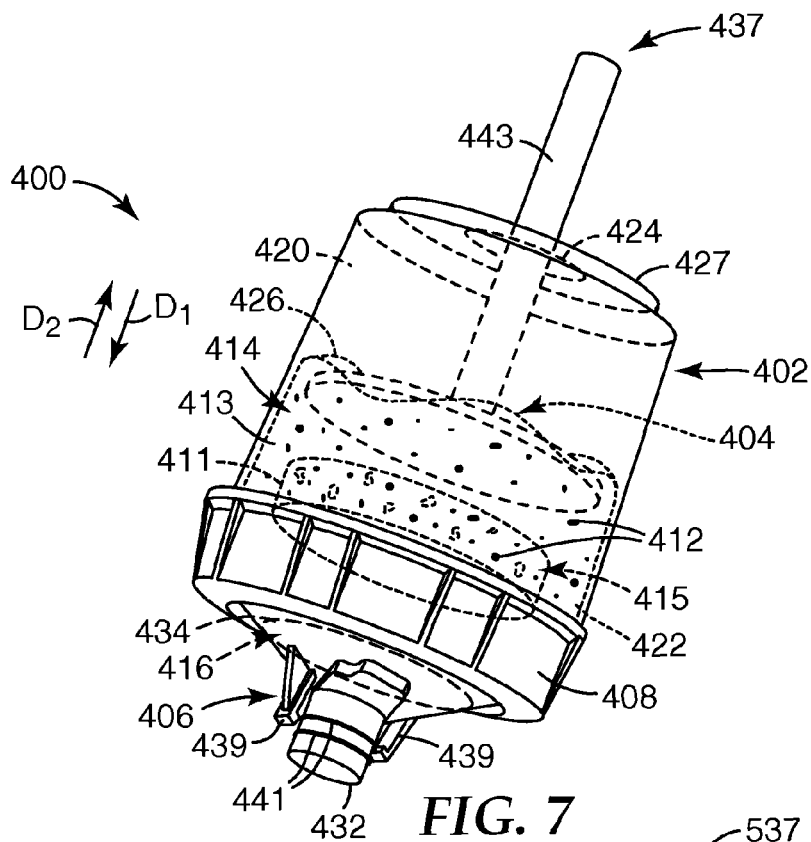
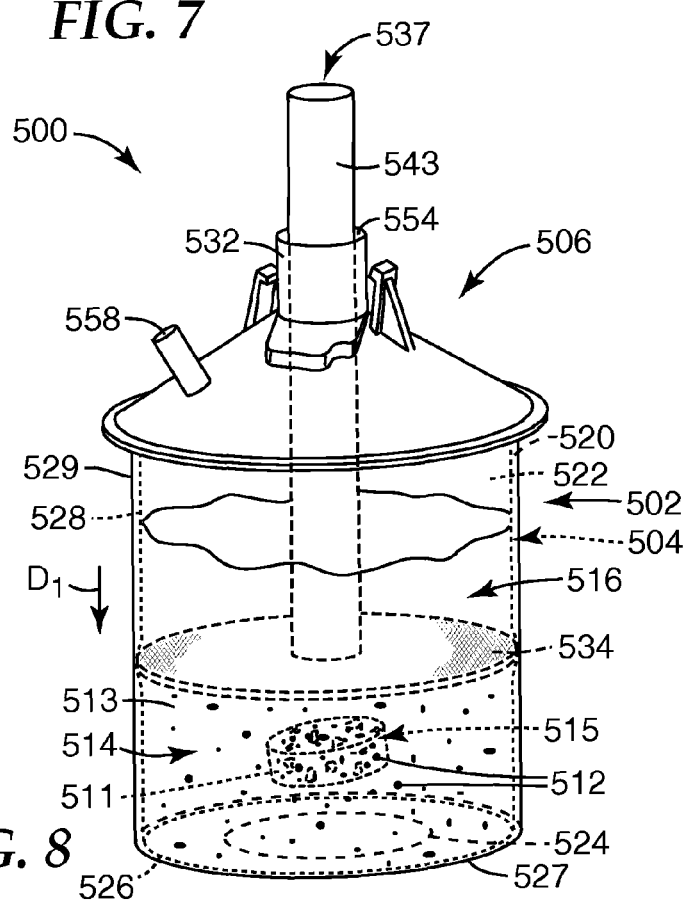

SAMPLE PREPARATION FOR ENVIRONMENTAL SAMPLING

CROSS REFERENCE TO RELATED APPLICATIONS

This application is a national stage filing under 35 U.S.C. 371 of PCT/US2008/084015, filed Nov. 19, 2008, which claims priority to U.S. Provisional Application No. 60/989,332, filed Nov. 20, 2007, the disclosure of which is incorporated by reference in its entirety herein.

BACKGROUND

When surfaces become contaminated with bacteria, fungi, yeasts, viruses, or other microorganisms (sometimes referred to as microbes), sickness (morbidity) and, sometimes, death (mortality) may result. This can be particularly true when surfaces in food processing plants and healthcare facilities (e.g., hospitals) become contaminated with microorganisms.

In food processing plants, surfaces (e.g., solid surfaces, equipment surfaces, protective clothing, etc.) may become contaminated. Such contamination may be caused by or transferred to meat or other foods. Such microbial contamination and/or transfer in certain environments may pose significant health risks. For example, the food that leaves a contaminated food processing plant will subsequently be eaten. Furthermore, foods grown, purchased and consumed by the general population may contain or acquire microorganisms, which can flourish or grow as a function of the environment in which they are located. This growth may lead to accelerated spoilage of the food product or to the proliferation of pathogenic organisms, which may produce toxins and/or cause infection.

In healthcare facilities, microorganisms may be released onto surfaces (e.g., solid surfaces, equipment surfaces, clothing, etc.) from infected individuals or otherwise. Once a surface becomes contaminated with microorganisms, contact with the contaminated surface may easily and readily transfer microorganisms to other locations, such as another surface, an individual, equipment, food, or the like. In addition, some of the patients of such facilities suffer from infections by pathogenic microbes and, thus, bring the pathogenic microbes into such facilities. Such microbial contamination and/or transfer can be particularly troublesome because many of those who are present in such facilities (e.g., patients) are sick and may be immunologically compromised. Such individuals therefore have an increased risk of becoming sick from infection by the contaminating microbes.

SUMMARY

Some embodiments of the present disclosure provide a system for preparing samples to test a surface for an analyte of interest. The system can include a deformable self-supporting receptacle comprising a reservoir, and a loaded substrate positioned in the reservoir of the deformable self-supporting receptacle. The loaded substrate can include a substrate and a source collected from the surface. The system can further include a diluent positioned in the reservoir of the deformable self-supporting receptacle in fluid communication with the loaded substrate, and a liquid composition positioned in the reservoir. The liquid composition can include the source and the diluent.

Some embodiments of the present disclosure provide a system for preparing samples to test a surface for an analyte of interest. The system can include a freestanding container comprising a first reservoir, a deformable self-supporting receptacle dimensioned to be received in the first reservoir of the freestanding container and comprising a second reservoir, and a lid coupled to at least one of the freestanding container and the deformable self-supporting receptacle. The freestanding container can be more rigid than the deformable self-supporting receptacle. The system can further include a loaded substrate positioned in the second reservoir of the deformable self-supporting receptacle, a diluent positioned in the second reservoir of the deformable self-supporting receptacle in fluid communication with the loaded substrate, and a liquid composition positioned in the second reservoir. The loaded substrate can include a substrate and a source collected from the surface. The liquid composition can include the source and the diluent.

Some embodiments of the present disclosure provide a method for preparing samples to test a surface for an analyte of interest. The method can include providing a loaded substrate. The loaded substrate can include a substrate and a source collected from the surface. The method can further include providing a sample preparation system comprising a deformable self-supporting receptacle comprising a reservoir, combining the loaded substrate and a diluent in the reservoir, and agitating the loaded substrate and the diluent to form a liquid composition comprising the source and the diluent.

Some embodiments of the present disclosure provide a method for preparing samples to test a surface for an analyte of interest. The method can include providing a loaded substrate, and providing a sample preparation system comprising a self-supporting receptacle. The loaded substrate can include a substrate and a source collected from the surface, and the self-supporting receptacle can include a reservoir and an inner surface. The method can further include positioning a diluent in the reservoir of the self-supporting receptacle, positioning the loaded substrate in the reservoir of the self-supporting receptacle, such that the loaded substrate is spaced a distance from the inner surface of the self-supporting receptacle, and such that the loaded substrate is in fluid communication with a diluent, and agitating the loaded substrate and the diluent to form a liquid composition comprising the source and the diluent.

Some embodiments of the present disclosure provide a method for preparing samples to test a surface for an analyte of interest. The method can include providing a loaded substrate, and providing a sample preparation system. The loaded substrate can include a substrate and a source collected from the surface. The sample preparation system can include a deformable self-supporting receptacle dimensioned to be received in a freestanding container. The freestanding container can be more rigid than the deformable self-supporting receptacle, and the deformable self-supporting receptacle can include a reservoir. The method can further include combining the loaded substrate and a diluent in the reservoir; agitating the loaded substrate and the diluent to form a liquid composition comprising the source and the diluent, and removing a sample from the sample preparation system.

Other features and aspects of the invention will become apparent by consideration of the detailed description and accompanying drawings.

BRIEF DESCRIPTION OF THE DRAWINGS

FIG. 7 is a perspective view of a sample preparation system according to another embodiment of the present disclosure.

FIG. 8 is a perspective view of a sample preparation system according to another embodiment of the present disclosure.

DETAILED DESCRIPTION

Figure 1:
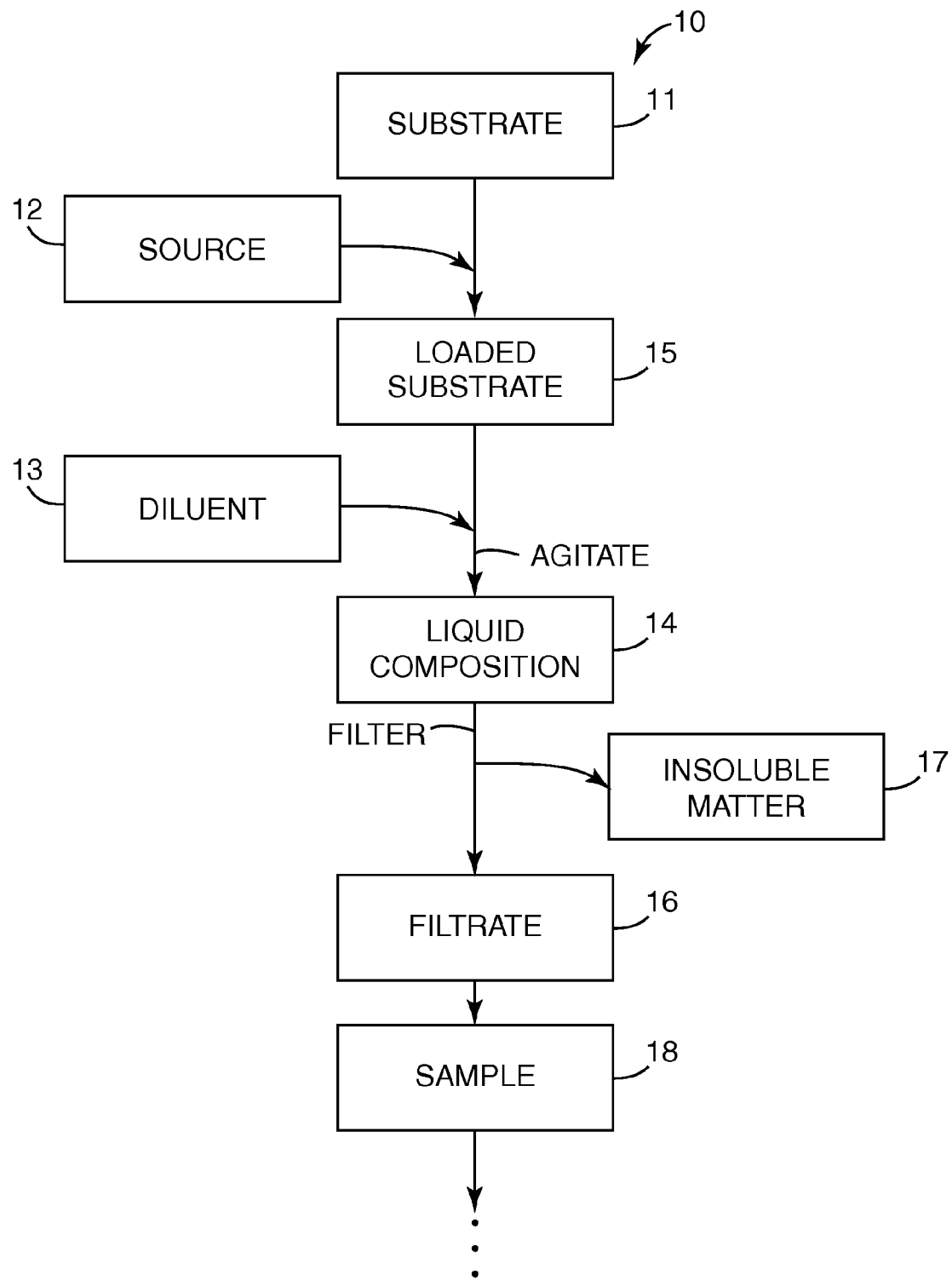
FIG. 1 is a schematic flow chart depicting a sample preparation method according to one embodiment of the present disclosure.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to a system and method for preparing samples to test an environmental surface for an analyte of interest. The samples can be further concentrated, enriched, and/or analyzed for the presence or absence of a variety of analytes.

The terms "surface" or "environmental surface" generally refers to any surface from which a source can be collected. The surface to be tested can be present in a variety of locations, including, but not limited to, healthcare facilities (e.g., hospitals, doctor offices, etc.), daycare facilities, schools, swimming pools, restrooms (e.g., commodes, sinks, shower stalls), locker rooms, fitness facilities (e.g., group fitness studios, gyms, etc.), long term care facilities (e.g., nursing homes), food processing plants, homes, offices, food service facilities, hotels, transportation vehicles (e.g., automobiles, buses, trains, airplanes, boats, cruise ships, etc.), etc. Examples of surfaces can include, but are not limited to, walls (including doors), floors, ceilings, drains, refrigeration systems, ducts (e.g., airducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. One or more surfaces can be sampled with one or more substrates, and the one or more substrates can be combined for testing.

The term "substrate" generally refers to a material used to collect samples from a surface of interest. The means of collection can include, but is not limited to, a charge interaction, a biochemical reaction (e.g., an antigen-antibody complex formation), absorption, adsorption, adhesion, cohesion, etc., and combinations thereof. The substrate is generally adapted to sample (i.e., collect a source from) large surface areas. For example, in some embodiments, the substrate is adapted to sample an area of at least 10 cm$^2$, in some embodiments, at least 100 cm$^2$, in some embodiments, at least 1 m$^2$, and in some embodiments, at least 100 m$^2$. The substrate can be in a variety of forms, including, but not limited to, a sponge, a wipe, a towel, a cloth, a mop head, a swab (e.g., a wound fiber product), a film, a brush (e.g., having rigid or deformable bristles), and the like, and combinations thereof. The substrate can be of a variety of sizes. For example, in some embodiments, the substrate is at least 10 cm$^2$, in some embodiments, at least 20 cm$^2$, in some embodiments, at least 50 cm$^2$, in some embodiments, at least 100 cm$^2$, in some embodiments, at least 150 cm$^2$, in some embodiments, at least 200 cm$^2$, and in some embodiments, at least 500 cm$^2$.

Suitable substrates can include, but are not limited to, woven materials, non-woven materials, porous materials, membranous materials, and combinations thereof. For example, suitable substrates can be formed of a variety of materials, including, but not limited to, polymers, papers, ceramics, metals, fabrics, adhesives, and combinations thereof. Specific examples of suitable substrates can include, but are not limited to foams; polymer films, such as polyethylene, polypropylene, or polyester; a dissolvable film or web (e.g., polyvinyl alcohol); a cellulosic material (e.g., a modified cellulose such as a cellulose ester (e.g., cellulose acetate) and a nitrocellulose); a woven web of one or more of the above materials (i.e., polymers, papers, ceramics, metals, fabrics, foams, polymer films, and combinations thereof); a nonwoven web of one or more of the above materials ((e.g., 3M™ THINSULATE™ insulation (3M Company, St. Paul, Minn.), 3M™ EASY TRAP™ duster system cloths (3M Company, St. Paul, Minn.), etc.); a metal-coated (e.g., vapor-coated) web, wherein the web includes one or more of the above materials; an adhesive-coated web, wherein the web includes one or more of the above materials; an electrostatically charged web, wherein the web includes one or more of the above materials; a fibrous web (e.g., blown microfibers, staple fibers, combinations thereof, etc.) of one or more of the above materials; or combinations thereof. In some embodiments, the substrate can further include a coating or a composition that renders it hydrophilic or hydrophobic. Various degrees of hydropilicity/hydrophobicity can be achieved. For example, in some embodiments, the coating or composition renders the substrate water-impervious.

In some embodiments, at least one major surface of the substrate is textured. The term "textured" generally refers to a relatively rough topology of a surface. For example, the texture of the major surfaces of a substrate may be relatively smooth. Alternatively, the texture of the major surfaces of the substrate may be relatively rough or "textured." In some embodiments, the substrate can include a major surface having one or more raised structures, including, but not limited to, bumps, spikes, ridges, and the like, or combinations thereof. In some embodiments, the substrate can include a major surface having one or more recessed structures, including, but not limited to, holes, pits, valleys, troughs, channels, microchannels, and the like, or combinations thereof. In some embodiments, at least one major surface of the substrate includes a combination of raised and recessed structures. In some embodiments, a substrate that includes raised structures, recessed structures, or a combination thereof, may provide an advantage in collecting material from an environmental surface by providing structures that can trap sample material and/or abrade and collect material from the surface of interest. Such raised or recessed structures may be integrally formed with the substrate, or such structures may be coupled to the substrate. Such raised or recessed structures may be formed, for example, by microreplication.

The term "source" is generally used to refer to material that is collected from a surface of interest to be tested for analytes. In some embodiments, the source is collected from a surface that appears to be clean, and thus, the contents of the source may not be visible to the naked human eye. In such embodiments, the source may only include small or microscopic materials, such as hair, skin cells, potential analytes of interest (e.g., microorganisms), dust, etc. However, in some embodiments, the source is collected from a surface that appears to be soiled. In such embodiments, the source can include food or non-food materials. The source can be a solid, a liquid, a semi-solid, a gelatinous material, and combinations thereof. Source material can be collected from all or a portion of a surface of interest. When a source is collected from a portion of a surface of interest, it is generally referred to as "sampling" the surface, or "taking a sample from the surface." However, the term "sample" is generally used herein to refer to a volume or mass of material that is extracted from the sample preparation system for further concentration, incubation, and/or analysis (e.g., detection of analytes).

The term "loaded substrate" is generally used to refer to a substrate that has picked up a source material from a surface of interest, such that the loaded substrate includes the substrate and the source. Depending on the type of substrate used and the type of source collected, the source can be present on the exterior (e.g., an outer surface) of the loaded substrate, and/or the source can be present in the interior (e.g., in channels or pores, which can be shallow or tortuous) of the loaded substrate.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, wood, soil, sediment, medicines, cosmetics, dietary supplements (e.g., ginseng capsules), pharmaceuticals, fomites, other suitable non-comestible materials, and combinations thereof.

The term "fomite" is generally used to refer to an inanimate object or substrate capable of carrying infectious organisms and/or transferring them. Fomites can include, but are not limited to, eating utensils, coins, paper money, cell phones, clothing (including shoes), doorknobs, feminine products, diapers, etc., portions thereof, and combinations thereof.

The term "analyte" is generally used to refer to a substance to be detected (e.g., by a laboratory or field test). A source can be tested for the presence or absence of particular analytes or for quantitation of particular analytes. Such analytes can be present within a source (e.g., on the interior), or on the exterior (e.g., on the outer surface) of a source. Examples of analytes can include, but are not limited to, microorganisms, parasites (some of which are also microorganisms), biomolecules, chemicals (e.g. pesticides, antibiotics), metal ions (e.g. mercury ions, heavy metal ions), metal-ion-containing complexes (e.g., complexes comprising metal ions and organic ligands), and combinations thereof.

A variety of testing methods can be used to identify and/or quantitate an analyte, including, but not limited to, microbiological assays, biochemical assays (e.g. immunoassay), or a combination thereof. Specific examples of testing methods that can be used include, but are not limited to, lateral flow assays, titration, thermal analysis, microscopy (e.g., light microscopy, fluorescent microscopy, immunofluorescent microscopy, scanning electron microscopy (SEM), transmission electron microscopy (TEM)), spectroscopy (e.g., mass spectroscopy, nuclear magnetic resonance (NMR) spectroscopy, Raman spectroscopy, infrared (IR) spectroscopy, x-ray spectroscopy, attenuated total reflectance spectroscopy, Fourier transform spectroscopy, gamma-ray spectroscopy, etc.), spectrophotometry (e.g., absorbance, fluorescence, luminescence, etc.), chromatography (e.g., gas chromatography, liquid chromatography, ion-exchange chromatography, affinity chromatography, etc.), electrochemical analysis, genetic techniques (e.g., polymerase chain reaction (PCR), transcription mediated amplification (TMA), hybridization protection assay (HPA), DNA or RNA molecular recognition assays, etc.), adenosine triphosphate (ATP) detection assays, immunological assays (e.g., enzyme-linked immunosorbent assay (ELISA)), cytotoxicity assays, viral plaque assays, techniques for evaluating cytopathic effect, culture techniques such as those that can be done using a growth medium (e.g., agar) and/or 3M™ Petrifilm™ Plates (e.g., and imaged, quantified and/or interpreted using a 3M™ Petrifilm™ Plate Reader (3M Company, St. Paul, Minn.)), other suitable analyte testing methods, or a combination thereof.

The term "microorganism" is generally used to refer to any prokaryotic or eukaryotic microscopic organism, including without limitation, one or more of bacteria (e.g., motile or vegetative, Gram positive or Gram negative), viruses (e.g., *Norovirus, Norwalk virus, Rotavirus, Adenovirus*, DNA viruses, RNA viruses, enveloped, non-enveloped, human immunodeficiency virus (HIV), human *Papillomavirus* (HPV), etc.), bacterial spores or endospores, algae, fungi (e.g., yeast, filamentous fungi, fungal spores), prions, mycoplasmas, and protozoa. In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacteria* spp. Particular examples of pathogens can include, but are not limited to, *Escherichia coli* including enterohemorrhagic *E. coli* e.g., serotype O157:H7, *Pseudomonas aeruginosa*, *Bacillus cereus*, *Bacillus anthracis*, *Salmonella enteritidis*, *Salmonella typhimurium*, *Listeria monocytogenes*, *Clostridium botulinum*, *Clostridium perfringens*, *Staphylococcus aureus*, methicillin-resistant *Staphylococcus aureus*, *Campylobacter jejuni*, *Yersinia enterocolitica*, *Vibrio vulnificus*, *Clostridium difficile*, vancomycin-resistant *Enterococcus*, and *Enterobacter sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

The term "parasite" is generally used to refer to an organism that lives in (i.e., an endoparasite) or on (i.e., an ectoparasite) a second organism (i.e., a host), and typically causes the second organism harm. Parasites can include, but are not limited to, microorganisms, and worms (e.g., roundworms, threadworms, hookworms, macroscopic multicellular worms, pinworms, whipworms, etc.). Specific examples of parasites can include, but are not limited to, *Cryptosporidium* spp., *Giardia* spp., *Blastocystis hominis*, *Endolimax nana*, *Cryptosporidium parvum*, *Entamoeba histolytica*, *Entamoeba coli*, *Entamoeba hartmanni*, *Giardia lamblia*, *Chilomastix mesnili*, *Cyclospora cayetanensis*, *Helminths* (macroscopic multicellular worms), *Ascaris lumbricoides* (human roundworm), *Strongyloides stercoralis* (threadworm), *Ancylostoma duodenale* (hookworm), *Necator americanus* (hookworm), *Enterobius vermicularis* (pinworm), and *Trichuris trichiura* (whipworm).

The term "biomolecule" is generally used to refer to a molecule, or a derivative thereof, that occurs in or is formed by an organism. For example, a biomolecule can include, but is not limited to, at least one of an amino acid, a nucleic acid, a polypeptide, a protein, a polynucleotide, a lipid, a phospholipid, a saccharide, a polysaccharide, and combinations thereof. Specific examples of biomolecules can include, but are not limited to, a metabolite (e.g., staphylococcal enterotoxin), an allergen (e.g., peanut allergen(s), egg allergen(s), pollens, dust mites, molds, danders, or proteins inherent therein, etc.), a hormone, a toxin (e.g., *Bacillus* diarrheal toxin, aflatoxin, *Clostridium difficile* toxin etc.), RNA (e.g., mRNA, total RNA, tRNA, etc.), DNA (e.g., plasmid DNA, plant DNA, etc.), a tagged protein, an antibody, an antigen, ATP, and combinations thereof.

The terms "soluble matter" and "insoluble matter" are generally used to refer to matter that is relatively soluble or insoluble in a given medium, under certain conditions. Specifically, under a given set of conditions, "soluble matter" is matter that goes into solution and can be dissolved in the solvent (e.g., diluent) of a system. "Insoluble matter" is matter that, under a given set of conditions, does not go into solution and is not dissolved in the solvent of a system. A source can include soluble matter and insoluble matter (e.g., cell debris). Insoluble matter is sometimes referred to as particulate(s) or debris and can include portions of the source material itself (i.e., from internal portions or external portions (e.g., the outer surface) of the source) or other source residue or debris resulting from an agitation process. The analyte of interest can be present in the soluble matter or the insoluble matter.

The term "agitate" and derivatives thereof is generally used to describe the process of giving motion to a liquid composition, for example, to mix or blend the contents of such liquid composition, or to liquefy a solid source by blending with a liquid. A variety of agitation methods can be used, including, but not limited to, manual shaking, mechanical shaking (e.g., linear shaking), sonicating (e.g., ultrasonic vibration), vortex stirring, manual stirring, mechanical stirring (e.g., by a mechanical propeller, a magnetic stirbar, or another agitating aid, such as ball bearings), manual beating, mechanical beating, blending, kneading, tumbling, and combinations thereof.

The term "filtering" is generally used to describe the process of separating matter by size, charge and/or function. For example, filtering can include separating soluble matter and a solvent (e.g., diluent) from insoluble matter, or it can include separating soluble matter, a solvent and relatively small insoluble matter from relatively large insoluble matter. A variety of filtration methods can be used, including, but not limited to, passing the liquid composition through a filter, settling followed by aspiration or decanting, other suitable filtration methods, and combinations thereof. "Settling" is used to refer to allowing the insoluble matter in the liquid composition to settle. Settling may occur by gravity or by centrifugation. The insoluble matter (or relatively large insoluble matter) can then be separated from the soluble matter (or soluble matter and relatively small insoluble matter) and solvent by aspirating the soluble matter and solvent from the insoluble matter, decanting the soluble matter and solvent, or a combination thereof.

A "filter" is generally used to describe the device used to separate the soluble matter (or soluble matter and relatively small insoluble matter) and solvent from the insoluble matter (or relatively large insoluble matter) in a liquid composition. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or non-uniform process, which can be calendered), a surface filter, a depth filter, a membrane (e.g., a ceramic membrane (e.g., ceramic aluminum oxide membrane filters available under the trade designation ANOPORE from Whatman Inc., Florham Park, N.J.), a polycarbonate membrane (e.g., track-etched polycarbonate membrane filters available under the trade designation NUCLEOPORE from Whatman, Inc.)), a polyester membrane (e.g., comprising track-etched polyester, etc.), a sieve, glass wool, a frit, filter paper, foam, etc., and combinations thereof.

The term "filtrate" is generally used to describe the liquid remaining after the insoluble matter (or at least the relatively large insoluble matter) has been removed from the liquid composition. Because filtering includes a broad range of methods, the term "filtrate" can also be used to refer to the supernatant that results from allowing insoluble matter (or relatively large insoluble matter) in a mixture to settle.

The term "remove" and derivatives thereof generally refers to the removal of a sample from the sample preparation system, but does not necessarily mean that the sample or the sample preparation system is exposed to ambience when it is removed. That is, a sample could be removed from the sample preparation system and moved directly into another device for concentration, incubation, analysis, etc. In some embodiments, the phrase "without exposing to ambience" and derivations thereof refers to not removing the sample from the sample preparation system (e.g., to prevent spills or contamination) until desired, but does not necessarily mean that the sample preparation system is closed to gas-exchange or that other liquids cannot get into the sample preparation and system, if desired.

FIG. 1 illustrates a sample preparation method 10 according to one embodiment of the present disclosure. The sample preparation method 10 can be used to prepare samples from a surface of interest that can be analyzed. As shown in FIG. 1, the sample preparation method 10 can begin by obtaining a substrate 11. The substrate 11 can then collect a source 12 from an environmental surface of interest to form a loaded substrate 15 comprising the source 12. A diluent 13 can be combined with all or a portion of the loaded substrate 15 and agitated to form a liquid composition 14 comprising the source 12 dissolved, dispersed, suspended and/or emulsified in the diluent 13. As such, the liquid composition 14 is generally a mixture, and can be a solution, an emulsion, a dispersion, a suspension, or a combination thereof. The substrate 11/loaded substrate 15 can remain in the presence of the liquid composition 14, or the substrate 11/loaded substrate 15 can be removed after a substantial amount of the source 12 has been released from the loaded substrate 15.

The substrate 11 can collect or pick up the source 12 from the surface of interest in a variety of ways, including directly contacting the surface and not directly contacting the surface of interest. For example, in some embodiments, the substrate 11 can be touched to the surface of interest to pick up the source 12. In some embodiments, the substrate 11 can be touched and moved along the surface to pick up the source 12. In some embodiments, the substrate 11 can be held near the surface of interest without touching the surface to pick up the source 12 (e.g., via an electrostatic charge). In some embodiments, the substrate 11 can be positioned near the surface and moved along the surface to pick up the source 12 (e.g., via an electrostatic charge). All of the above collection methods will be generally referred to herein as "collecting" the source from the surface.

The source 12, when combined with the diluent 13, can include soluble matter and insoluble matter 15, such that some portions of the source 12 can be dissolved in the diluent 13, while other portions of the source 12 are suspended, dispersed or emulsified in the diluent 13. The liquid composition 14 is then filtered to form a filtrate 16 that comprises the analyte of interest (if present). The analyte of interest can be present in the soluble matter or the insoluble matter of the liquid composition 14. If the analyte of interest is present in the insoluble matter, and if a filter is employed to remove the analyte of interest from debris or unwanted material, the filter is typically adapted to allow the analyte of interest (and perhaps other similarly-sized insoluble matter) to pass through the filter as filtrate 16, while restricting relatively large insoluble matter 17 from passing through the filter. Therefore, it should be understood that the filtrate 16 can also include some insoluble matter, and insoluble matter 17 is shown in FIG. 1 as being removed from the liquid composition 14 for simplicity and by way of example only. A sample 18 can then be formed from at least a portion of the filtrate 16, and the sample 18 can be removed for concentration, incubation, analysis, etc. Samples 18 from a variety of sample preparation systems can be pooled together for one or more of enrichment, concentration, analysis, etc.

Throughout the present disclosure, one or more of the liquid composition 14, the filtrate 16, and any samples 18 thereof, may be described as including the analyte of interest. However, in some embodiments, the liquid composition 14 may not include the analyte of interest and may lead to a negative test result when the sample is analyzed. For example, if a sample is prepared and tested for a bacterium, and the surface from which the source was originally collected did not include that bacterium, the liquid composition 14 formed in the above process, and any filtrates 16 and samples 18 thereof will also not include that bacterium of interest. Thus, even if one or more of the liquid composition 14, the filtrate 16, and any samples 18 taken therefrom are described as including the analyte of interest, it should be understood that this would only be the case if the analyte of interest was present.

The sample preparation method 10 illustrated in FIG. 1 and described above is illustrated and described by way of example only. However, one of ordinary skill in the art should understand that the sample preparation method of the present disclosure need not include every step illustrated in FIG. 1 and described above. For example, in some embodiments of the present disclosure, the sample preparation method 10 does not include the filtering step, but rather a sample of the liquid composition 14 is concentrated, incubation, and/or analyzed, etc.

The diluent 13 is generally a liquid and, in some embodiments, is a sterile liquid. In some embodiments, the diluent 13 can include a variety of additives, including, but not limited to, surfactants, or other suitable additives that aid in dispersing, dissolving, suspending or emulsifying the source for subsequent analyte testing; rheological agents; antimicrobial neutralizers (e.g., that neutralize preservatives or other antimicrobial agents); enrichment or growth medium comprising nutrients (e.g., that promote selective growth of desired microorganism(s)) and/or growth inhibitors (e.g., that inhibit the growth of undesired microorganism(s)); pH buffering agents; enzymes; indicator molecules (e.g. pH or oxidation/reduction indicators); spore germinants; an agent to neutralize sanitizers (e.g., sodium thiosulfate neutralization of chlorine); an agent intended to promote bacterial resuscitation (e.g., sodium pyruvate); or a combination thereof. In some embodiments, the diluent 13 includes sterile water (e.g., sterile double-distilled water ($ddH_2O$)); one or more organic solvents to selectively dissolve, disperse, suspend, or emulsify the source; aqueous organic solvents, or a combination thereof. In some embodiments, the diluent 13 is a sterile buffered solution (e.g., Butterfield's Buffer, available from Edge Biological, Memphis Tenn.). In some embodiments, the diluent 13 is a selective or semi-selective nutrient formulation, such that the diluent 13 may be used in the selective or semi-selective growth of the desired analyte(s) (e.g., bacteria). In such embodiments, the diluent 13 can be incubated with the source 12 for a period of time (e.g., at a specific temperature) to promote such growth of the desired analyte(s).

Examples of growth medium can include, but are not limited to, Tryptic Soy Broth (TSB), Buffered Peptone Water (BPW), Universal Pre-enrichment Broth (UPB), Listeria Enrichment Broth (LEB), Lactose Broth, Bolton broth, or other general, non-selective, or mildly selective media known to those of ordinary skill in the art. The growth medium can include nutrients that support the growth of more than one desired microorganism (i.e., analyte of interest).

Examples of growth inhibitors can include, but are not limited to, bile salts, sodium deoxycholate, sodium selenite, sodium thiosulfate, sodium nitrate, lithium chloride, potassium tellurite, sodium tetrathionate, sodium sulphacetamide, mandelic acid, selenite cysteine tetrathionate, sulphamethazine, brilliant green, malachite green oxalate, crystal violet, Tergitol 4, sulphadiazine, amikacin, aztreonam, naladixic acid, acriflavine, polymyxin B, novobiocin, alafosfalin, organic and mineral acids, bacteriophages, dichloran rose bengal, chloramphenicol, chlortetracycline, certain concentrations of sodium chloride, sucrose and other solutes, and combinations thereof.

In some embodiments, the source 12 includes the diluent 13, such that the liquid composition 14 includes the source 12 and the diluent 13, but the diluent 13 was not added separately. For example, a food source that includes a substantial amount of water or other liquid can be mixed to form the liquid composition 14 comprising the source 12 and the diluent 13, without requiring the addition of a separate diluent 13. In some embodiments, the source 12 may be substantially dissolved in the diluent 13, such that the liquid composition 14 includes a minimal amount of insoluble matter 15, making the filtering step unnecessary.

In some embodiments, the loaded substrate 15 includes the diluent 13. For example, in some embodiments, the loaded substrate 15 can include the diluent 13 because the substrate 11 (i.e., prior to collecting the source 12) includes the diluent 13 (e.g., the substrate 11 is prepackaged wet or is pre-wet with the diluent 13 prior to collecting the source 12). In such embodiments, for example, the substrate 11 can include a wetting agent or a surfactant (e.g., to facilitate the removal of the source 12 from the surface of interest, or to facilitate the capture of the source 12 by the substrate 11), an agent to neutralize sanitizers (e.g., sodium thiosulfate neutralization of chlorine) or an agent intended to promote bacterial resuscitation (e.g., sodium pyruvate). In some embodiments, the loaded substrate 15 can include the diluent 13 as a result of the diluent 13 being added to the loaded substrate 15 (i.e., after collecting the source 12; e.g., rinsing the loaded substrate 15 with the diluent 13). In some embodiments, the loaded substrate 15 can include the diluent 13 as a result of the source 12 and the diluent 13 both being present on the surface to be tested and both being picked up by the substrate 11. In some embodiments, the loaded substrate 15 can include the diluent 13 because the source 12 that is picked up by the substrate 11 includes the diluent 13. In some embodiments, the loaded substrate 15 includes the diluent 13 as a result of a combination of one or more of the above scenarios.

Figure 2:
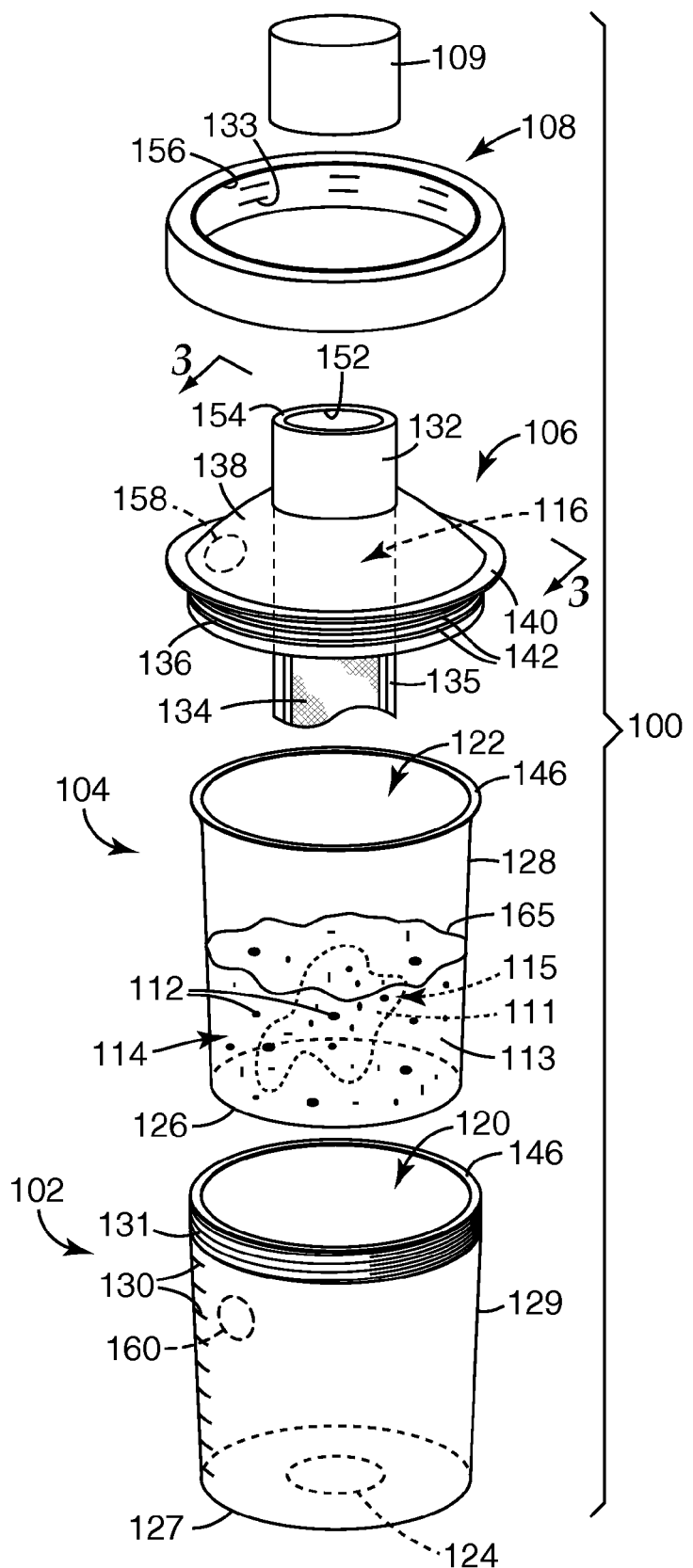
FIG. 2 is an exploded perspective view of a sample preparation system according to one embodiment of the present disclosure, the sample preparation system including a lid.

FIG. 2 illustrates a sample preparation system 100 according to one embodiment of the present disclosure. As shown in FIG. 2, the sample preparation system 100 includes a container 102, a liner 104, a lid 106, a collar 108, and a cover 109. In some embodiments, one or more of the components of the sample preparation system 100 are sterile or sterilizable by sterilization and disinfection procedures such as steam, gamma radiation, ethylene oxide, hydrogen peroxide, peracetic acid, hydro-alcoholic solutions, bleach, and combinations thereof. A system having similar features to that of the sample preparation system 100 is described in PCT Publication No. WO 98/32539, U.S. Pat. No. 6,536,687 and U.S. Pat. No. 6,588,681, PCT Publication No. 2004/060574, PCT Publication No. 2004/060575, US Publication No. 2004/0164182, PCT Publication No. 2004/094072, PCT Publication No. WO 2007/079143, PCT Publication No. WO 2007/079188, each of which is incorporated herein in its entirety by reference.

Some embodiments of the present disclosure employ a plurality of sample preparation systems 100 to allow multiple sample preparation systems 100 be employed in parallel (or to have samples pooled) to expedite sample preparation and increase productivity/output. In such embodiments, the plurality of sample preparation systems 100 can be at least partially integrally formed, or they can be separately formed. For example, in some embodiments, multiple liners 104 can be used in one relatively large container 102 (e.g., with multiple reservoirs for the liners 104).

In some embodiments, as shown in FIG. 2, the container 102 is freestanding and/or self-supporting and includes a base 127 and a sidewall 129. The term "freestanding" is generally used to refer to an object that is capable of standing on its own without collapsing or distorting, and without being held by another object. The term "self-supporting" is generally used to refer to an object that does not collapse or deform under its own weight. For example, a bag is typically not "self-supporting" in that it does not maintain its shape, but rather collapses or distorts, under its own weight. A self-supporting object is not necessarily freestanding.

The container 102 can be formed of a variety of materials including, but not limited to, polymeric materials, metals (e.g., aluminum, stainless steel, etc.), ceramics, glasses, and combinations thereof. Examples of polymeric materials can include, but are not limited to, polyolefins (e.g., polyethylene, polypropylene, combinations thereof, etc.), polycarbonate, acrylics, polystyrene, high density polyethylene (HDPE), polypropylene, other suitable polymeric materials capable of forming a freestanding and/or self-supporting container, or a combination thereof. The container 102 can be translucent (or even transparent), or opaque, and can be any suitable size, depending on the type, amount and size of source/loaded substrate to be analyzed. For example, in some embodiments, the container 102 can have a capacity of 50 mL, 100 mL, 250 mL, or larger.

In some embodiments, as shown in FIG. 2, the sample preparation system 100 includes a liner 104, which is shaped and dimensioned to be received within the container 102. The liner 104 can be disposable (e.g., made for one-time use), to allow the container 102 to be reused without substantial risk of contamination and without extensive cleaning required between uses. As described in greater detail below and illustrated in FIG. 9, in some embodiments, the sample preparation system includes a liner without a container. When the liner is used without a container, it is not functioning as a "liner," per se, and can be referred to generally as a receptacle or container.

As shown in FIG. 2, the container 102 defines a first reservoir 120, and the liner 104 defines a second reservoir 122. The liner 104 is shaped and dimensioned to be received within the first reservoir 120 of the container 102. In some embodiments, a diluent 113 and a loaded substrate 115 comprising a substrate 111 and a source 112 can be added to the first reservoir 120. In some embodiments, as shown in FIG. 2, the liner 104 is employed, and the loaded substrate 115 and the diluent 113 are positioned within the second reservoir 122, and the liner 104 is positioned within the first reservoir 120. Whether added to the first reservoir 120 or the second reservoir 122, the loaded substrate 115 and the diluent 113 can be combined (and agitated) to form a liquid composition 114 comprising the source 112 and the diluent 113. In some embodiments, the liner 104 is freestanding, and the liner 104 or the container 102 can serve as a freestanding receptacle that can contain the liquid composition 114 and the loaded substrate 115.

In the embodiment illustrated in FIG. 2, the loaded substrate 115 includes a substrate 111, and the substrate 111 is in the form of a wipe. The wipe can be smooth or textured and can be formed of any of the above-described materials. The wipe is shown in FIG. 2 by way of example only, but it should be understood that the substrate 111 can be formed of any of the above-described materials and can be in any of the above-described forms without departing from the spirit and scope of the present disclosure.

At the point in time shown in FIG. 2, it can be assumed that the substrate 111 was already used to collect the source 112 from a surface of interest to form the loaded substrate 115, and the loaded substrate 115 was positioned in the second reservoir 122 of the liner 104. As the loaded substrate 115 is mixed with the diluent 113, the source 112 can be combined with the diluent and removed from the loaded substrate 115, which may lead to the loaded substrate 115 being "unloaded." Whether the loaded substrate 115 is still "loaded" with the source 112 or has been partially or completely "unloaded" will depend on a variety of factors, such as the equilibria with the liquid composition 114, what type of source 112 was collected, and what point in time it is. Therefore, for simplicity, the substrate will be described as the loaded substrate 115 if it has already collected the source 112 and when it is positioned in the sample preparation system 100. However, it should be understood that the loaded substrate 115 can become "unloaded" as the loaded substrate 115 is in the presence of the diluent 113 and as the liquid composition 114 is formed.

The loaded substrate 115 can be added to the container 102 or the liner 104 first, followed by addition of the diluent 113, the diluent 113 can be added first, followed by the loaded substrate 115, or the loaded substrate 115 and the diluent 113 can be added simultaneously (or the loaded substrate 115 and/or the source 112 can include the diluent 113). Alternatively, the loaded substrate 115 and the diluent 113 can be combined prior to being added to the sample preparation system 100. In some embodiments, the diluent 113 can be applied to (e.g., by spraying, pouring, etc.) the surface to be tested prior to using the substrate 111 to collect the source 112, such that as the substrate 111 collects the source 112, it also collects the diluent 113, and the loaded substrate 115 comprising the source 112 and the diluent 113 can be added to the sample preparation system 100.

In some embodiments in which the diluent 113 is added to the container 102 or the liner 104 first, a pre-measured amount of the diluent 113 (e.g., a sterile liquid diluent) can be sealed in the container 102 or the liner 104 with a removably coupled cover (e.g., a one-time use removable barrier film that is coupled to the container 102 or the liner 104 by one or more of an adhesive, heat sealing, ultrasonic welding, or any of the other coupling means described below), so that the cover can be removed just prior to adding the loaded substrate 115. Alternatively, in some embodiments, a pre-measured amount of a dry powdered media (e.g., nutrient media for analyte(s) of interest and/or growth inhibitors for analyte(s) not of interest) can be sealed in the container 102 or the liner 104 with a removably coupled cover, or the desired media can be coated or adsorbed onto an inner surface of the container 102 or the liner 104. In such embodiments, the cover can be removed and a solvent (e.g., ddH$_2$O) can be added to form the diluent 113, either prior to or at the same time as the loaded substrate 115 is added. Alternatively, if the source 112 and/or the loaded substrate 115 includes enough of a liquid capable of dissolving the media, the loaded substrate 115 can be added to the dry powdered media to form the liquid composition 114 that comprises the source 112 and a diluent 113 (e.g., the media dissolved in a solvent provided by the source 112 and/or the loaded substrate 115).

In some embodiments, the container 102 and/or the liner 104 (if the liner 104 is employed) can be compartmentalized to include more than one first reservoir 120 and/or more than one second reservoir 122, respectively. Multiple reservoirs 120/122 can be used, for example, for multi-stage enrichment, for parallel or simultaneous enrichment of different microorganisms, or a combination thereof. By way of example, the liner 104 can include two second reservoirs 122 (referred to in this example as reservoir A and B for simplicity). A first enrichment media can be positioned in reservoir A for primary enrichment of a microorganism, and a second enrichment media can be positioned in reservoir B for secondary enrichment of the same microorganism. Reservoirs A and B can be positioned, for example, such that both are accessible for positioning of the media but that the loaded substrate 115, or a portion thereof, and the diluent 113 can be added to one without being added to the other. After the liquid composition 114 has been formed and primary enrichment has occurred in reservoir A, any portion of the liquid composition 114 (and optionally the loaded substrate 115) can be moved to reservoir B for secondary enrichment. The liquid composition 114, or a portion thereof, can be moved to reservoir B in a variety of ways, including agitation of the sample preparation system 100, breaking of a frangible barrier between the two reservoirs A and B, etc.

In some embodiments, one container 102 can be employed with a plurality of liners 104, such that one container 102 can include one or more first reservoirs 120, and/or one or more liners 104 (each including one or more second reservoirs 122) can be positioned in the container 102. Other configurations are possible, and one of ordinary skill in the art will recognize the different permutations possible for achieving multiple compartments. No matter what the configuration, the multiple reservoirs or compartments can be positioned side-by-side, vertically, concentrically, or a combination thereof.

In some embodiments, the loaded substrate 115 can be at least partially broken apart in forming the liquid composition 114 and in attempting to remove the source 112 from the loaded substrate 115. Breaking up the loaded substrate 115 can increase the concentration of the source 112 in the liquid composition 114. For example, agitation processes can be employed that will break apart or cut the loaded substrate 115 to increase the surface area available for the diluent 113 to interact with or enter the loaded substrate 115. In some embodiments, the loaded substrate 115 can include a relatively delicate substrate 111 that facilitates the breakdown of the loaded substrate 115. In addition, in some embodiments, the diluent 113 can include physical or chemical agents adapted to facilitate the physical or chemical breakdown of the loaded substrate 115. For example, in some embodiments, the diluent 113 can include a solvent capable of dissolving the substrate 111 (e.g., the substrate 111 is dissolvable in water).

The liner 104 can be formed of a variety of materials, including a variety of polymeric materials, including, but not limited to, a polyolefin, including, but not limited to polypropylene (e.g., low density polyethylene (LDPE)), polyethylene, and poly(methylpentene), polyamide (e.g., NYLON®), or a combination thereof. In some embodiments, the liner 104 is formed from a molding process, such as a thermoforming process. The liner 104 can be translucent (or even transparent), or opaque.

In some embodiments, as illustrated in FIG. 2, the liner 104 is freestanding and/or self-supporting, either of which can allow the loaded substrate 115 and diluent 113 to be loaded into the liner 104 prior to positioning the liner 104 within the container 102, without the liner 104 collapsing or distorting. In addition, a freestanding and/or self-supporting liner 104 can aid in weighing, loaded substrate 115 and/or diluent 113 addition, transporting, handling, and/or sample removal.

In some embodiments, the liner 104 is self-supporting and/or freestanding while also being deformable. The term "deformable" is used to refer to a structure that can be altered from its original shape or state by pressure (e.g., positive or negative) or stress. In embodiments employing a deformable liner 104, pressure can be applied to the liner 104 to reduce its size from its original (i.e., unstressed) dimensions. Such pressure can be used to promote removal of the liquid composition 114 (or a filtrate thereof) from the liner 104. In such embodiments, the liner 104 can serve as a deformable self-supporting receptacle that can contain the liquid composition 114. In some embodiments, the deformable self-supporting receptacle is also freestanding.

In some embodiments, as shown in FIG. 2, the container 102 includes an aperture 124 formed in its base 127, through which a user can access the liner 104 to apply pressure to the liner 104 to cause it to deform. Such pressure can be applied directly by hand, or by an additional device, and could be a manual or automated process. The aperture 124 can be shaped and dimensioned according to the desired application of use. In some embodiments, base 127 of the container 102 is nothing more than the bottom of the sidewall 129, or a slight inward projection of the sidewall 129, such that the liner 104 is easily accessible at the bottom of the container 102. Said another way, in some embodiments, the aperture 124 of the container 102 defines a majority of the bottom of the container 102 (e.g., a majority of the cross-sectional area of the container 102), and the base 127 is only a small portion of the container 102 surrounding the aperture 124. In embodiments that do not employ the liner 104, the container 102 need not include the aperture 124.

In some embodiments, the liner 104 includes a relatively rigid base 126 and a relatively thin and deformable sidewall 128, such that when pressure is applied to the base 126 in a direction parallel to the longitudinal axis of the liner 104 (e.g., via the aperture 124 in the container 102), the liner 104 deforms in the longitudinal direction (e.g., by virtue of the sidewall 128 collapsing rather than the base 126). Alternatively, or in addition, the base 126 can be thicker than the sidewall 128. By way of example only, in some embodiments, the thickness of the sidewall 128 is at least 50 μm, in some embodiments, at least 100 μm, in some embodiments, at least 150 μm, and in some embodiments, at least 200 μm. In some embodiments, the thickness of the base 126 is at least 225 μm, in some embodiments, 275 μm, in some embodiments, at least 300 μm, and in some embodiments, at least 350 μm.

The liner 104 can further include one or more of baffles, pleats, corrugations, seams, joints, gussets, weakened portions (e.g., annular weakened portions), or a combination thereof, which may be incorporated to assist in controlling the deformability of the liner 104, and/or can further reduce the internal volume of liner 104. In some embodiments, as described in greater detail below and illustrated in FIG. 9, the liner 104 includes an accordion-type configuration. In some embodiments, liner 104 does not include any grooves on its internal surface, particularly, at the internal junction between the base 126 and the sidewall 128.

In some embodiments, the liner 104 is deliberately deformed to impart a disruption to the surface geometry of the liner 104. Such a disrupted surface geometry can assist in the breakup of the source 112 and/or the loaded substrate 115 during agitation. For example, in some embodiments, an obstruction (e.g., a relatively rigid material) can be positioned between the sidewall 128 of the liner 104 and the container 102 to create a different surface geometry in the sidewall 128 of the liner 104.

As shown in FIG. 2, the container 102 can include indicia 130 to indicate the level (i.e., volume) of contents within the container 102. One example of suitable indicia is described in U.S. Pat. No. 6,588,681. Alternatively, or in addition, the liner 104 can include indicia. To enable the use of the indicia 130 on the container 102 and/or the liner 104, the container 102 and/or the liner 104 can be translucent, or even transparent to be able to see the contents through the sidewall 129 of the container 102 and/or the sidewall 128 of the liner 104. The sidewalls 128 and 129 may also bear other types of markings, such as trademarks, brand names, and the like. The indicia 130 can also be provided on a film that is dimensioned to be received within the container 102 or the liner 104 and which can be formed of a material that includes sufficient internal stresses to cause the film to press outwardly (i.e., radially) against an inner surface of the container 102 or the liner 104.

In the embodiment illustrated in FIG. 2, the lid 106 is removably coupled to the liner 104, and the collar 108 is employed to further secure the lid 106 to the container 102. For example, in FIG. 2, the container 102 includes threads 131 at the upper end of the outer surface of the sidewall 129, which are shaped and dimensioned for the collar 108 (having internal threads 133 capable of engaging with the threads 131 on the container 102) to be screwed onto the upper end of the container 102. As an alternative to using the collar 108 for securing the lid 106 to the container 102, other coupling means can be employed including clamping and/or any of the other coupling means described below. In some embodiments, the liner 104 is not employed, and the lid 106 can be coupled directly to the container 102. In such embodiments, the collar 108 need not be employed. Thus, the lid 106 can form a seal (e.g., a hermetic seal) with either the container 102 or the liner 104. In some embodiments, the lid 106 and the container 102 (or the lid 106 and the liner 104) are integrally formed or permanently coupled together.

A variety of coupling means can be employed either between the lid 106 and the liner 104, the lid 106 and the container 102, and/or the collar 108 and the container 102 to allow the respective components to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the sample preparation system 100 need not be reopened after the source 112 and the diluent 113 are added, such that the container 102, the liner 104, the lid 106 and the collar 108 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

Figure 3:
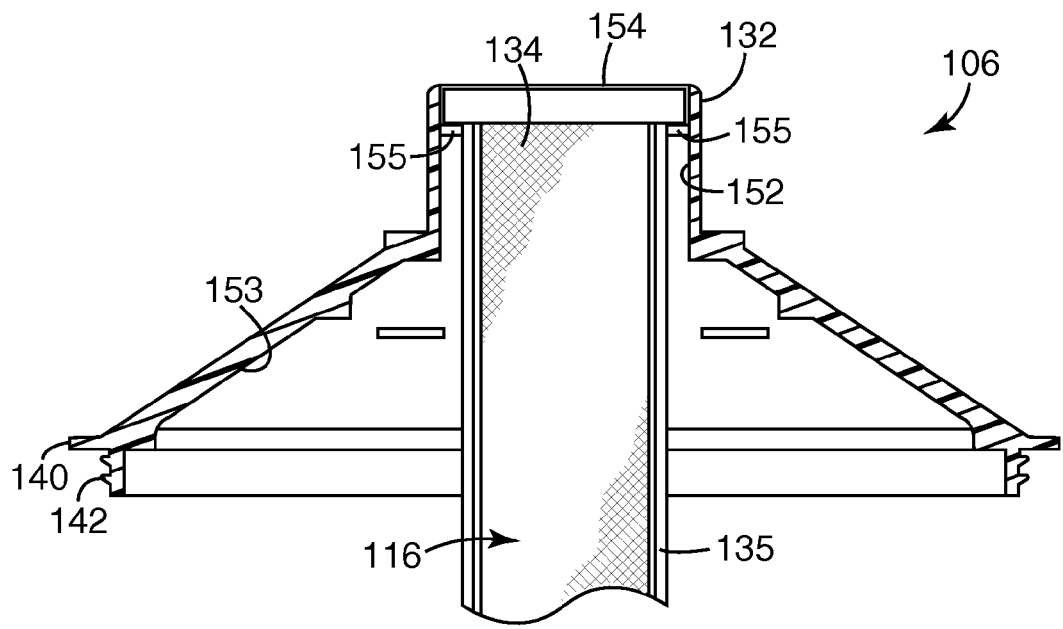
FIG. 3 is close-up cross-sectional view of the lid of FIG. 2, taken along line 3-3 in FIG. 2.

As shown in FIGS. 2 and 3, the lid 106 further includes a port 132, which can be coupled to a filter 134, a cylindrical portion 136 that is dimensioned to be received within the liner 104, and a generally conical (e.g., frusto-conical) portion 138 that extends from the cylindrical portion 136 to the port 132. At the junction between the cylindrical portion 136 and the conical portion 138, the lid 106 further includes a lip 140 that extends radially outwardly from the cylindrical portion 136 and the conical portion 138.

In some embodiments, the filter 134 is coupled directly to the lid 106. In some embodiments, as shown in FIGS. 2-3, the filter 134 can be supported by a frame 135 and coupled to the lid 106 via the frame 135. The frame 135 can form a portion of the filter 134, the frame 135 can be a part of the lid 106, or the frame 135 can be a separate element that is coupled to both the filter 134 and the lid 106. The frame 135 can be formed of a variety of materials, including, but not limited to, a variety of polymers, metals, ceramics, glasses, and combinations thereof. In the embodiment illustrated in FIGS. 2-3, the filter 134 is formed of a metal mesh, and the frame 135 is formed of a polymer that is bonded to the metal filter 134. The frame 135 is coupled to the lid 106, as described in greater detail below.

The filter 134 and the frame 135 of the embodiment illustrated in FIGS. 2 and 3 are shaped and dimensioned so as to extend below the bottom end of the lid 106, such that when the sample preparation system 100 is assembled, the filter 134 and the frame 135 extend into the second reservoir 122 of the liner 104 (or the first reservoir 120 of the container 102). However, the filter 134 and frame 135 can take on a variety of shapes and sizes. In some embodiments, for example, the frame 135 can include a rigid upper portion (e.g., that is coupled to the lid 106) and a rigid lower portion, and the filter 134 can be coupled therebetween, and the filter 134 can be collapsible. Such an embodiment is described in greater detail below and illustrated in FIG. 9.

The cylindrical portion 136 of the lid 106 includes a plurality of circumferential outwardly-projecting protrusions 142 to allow the cylindrical portion 136 to be snap-fit or press-fit to the inner surface of the liner 104. In some embodiments, the inner surface of the liner 104 can include inwardly-projecting protrusions that are used either in lieu of the outwardly-projecting protrusions 142, or in addition to the outwardly-projecting protrusions 142 (e.g., to form a mating relationship therewith).

The liner 104 can include a lip 144 that projects radially outwardly from the sidewall 128 of the liner 104, and which can form an abutting relationship with an upper surface 146 of the container 102 and the lip 140 of the lid 106, such that when the sample preparation system 100 is assembled, the lip 144 of the liner 104 is positioned between the lip 140 of the lid 106 and the upper surface 146 of the container 102, and a seal (e.g., a hermetic seal) is formed. As shown in FIG. 2, the collar 108 includes an inwardly-projecting lip 156, such that when the collar 108 is coupled to the container 102, the lip 156 of the collar 108 presses the lip 140 of the lid 106 into contact with the lip 144 of the liner 104, which is pressed into contact with the upper surface 146 of the container 102 (e.g., to form a higher integrity seal). The above-described means for assembling the sample preparation system 100 and for forming a seal between the components of the sample preparation system 100 are described and illustrated by way of example only. One of ordinary skill in the art will understand, however, that a variety of other mechanisms could be employed to assemble the components of the sample preparation system 100 and to form a seal (e.g., a liquid-tight seal, a hermetic seal, or a combination thereof), such that the sample preparation system 100 is inhibited from leaking under normal operating conditions.

While the lid 106 of the embodiment illustrated in FIGS. 2 and 3 is illustrated as having a generally conical or frusto-conical shape. It should be understood that the lid 106 could have a variety of other shapes, including, but not limited to, a cylindrical shape, a tubular shape having a rectangular or square cross-sectional area, or other shapes suitable to being coupled to the other components of the sample preparation system 100. Similarly, the container 102, the liner 104, and the collar 108 could have a variety of other shapes than the substantially cylindrical shapes illustrated in FIG. 2. In addition, the lid 106 can be dimensioned to accommodate the other components of the sample preparation system 100.

The lid 106 can be formed of a variety of materials, including the materials listed above with respect to the container 102. The lid 106 can be translucent (or even transparent), or opaque, depending on the application of use.

The collar 108 can be formed of a variety of materials, including, but not limited to a variety of polymeric materials, metal materials, and combinations thereof. For example, the collar 108 can be formed of a molded plastic component, or a machined metal (such as aluminum) component. In some embodiments, the collar 108 is formed of a molded plastic component comprising glass fiber reinforced polypropylene.

As shown in FIG. 2, the port 132 of the lid 106 is generally cylindrical and tubular in shape, such that the port 132 defines a portion 152 of the inner surface 153 of the lid 106 and an opening 154 in the lid 106. The lid 106 is hollow and is in fluid communication with the second reservoir 122 when the sample preparation system 100 is assembled. The port 132 does not need to be cylindrical and can instead take on any shaped necessary for a given application. In the embodiment illustrated in FIGS. 2 and 3, the filter 134 is coupled to the port 132 (i.e., via the frame 135) such that the filter 134 is in fluid communication with the lid opening 154, as well as the second reservoir 122.

In the embodiment shown in FIG. 2, the cover 109 is shaped and dimensioned to receive at least a portion of the port 132. As a result, the cover 109 can be coupled to the port 132 of the lid 106 to close the opening 154 in the lid 106 and to seal (e.g., hermetically seal) the sample preparation system 100 from the environment. The cover 109 can be coupled to the lid 106 using any of the above-described coupling means. The cover 109 can be integrally formed with the lid 106 (e.g., a flip-top snap-on cover, as described in greater detail below and illustrated in FIG. 13), or the cover 109 can be separate from the lid 106 (e.g., a screw-on cover, as described in greater detail below and illustrated in FIGS. 9-12). The cover 109 can be formed of a variety of materials, including the materials listed above with respect to the container 102 or the collar 108.

In some embodiments, the lid 106 includes a frangible or penetrable barrier or a removable film separating at least a portion of the interior of the lid 106 from the environment, such that the barrier can be punctured or pierced or the film removed to access the interior of the lid 106. In such embodiments, the cover 109 need not be employed.

Figure 5:
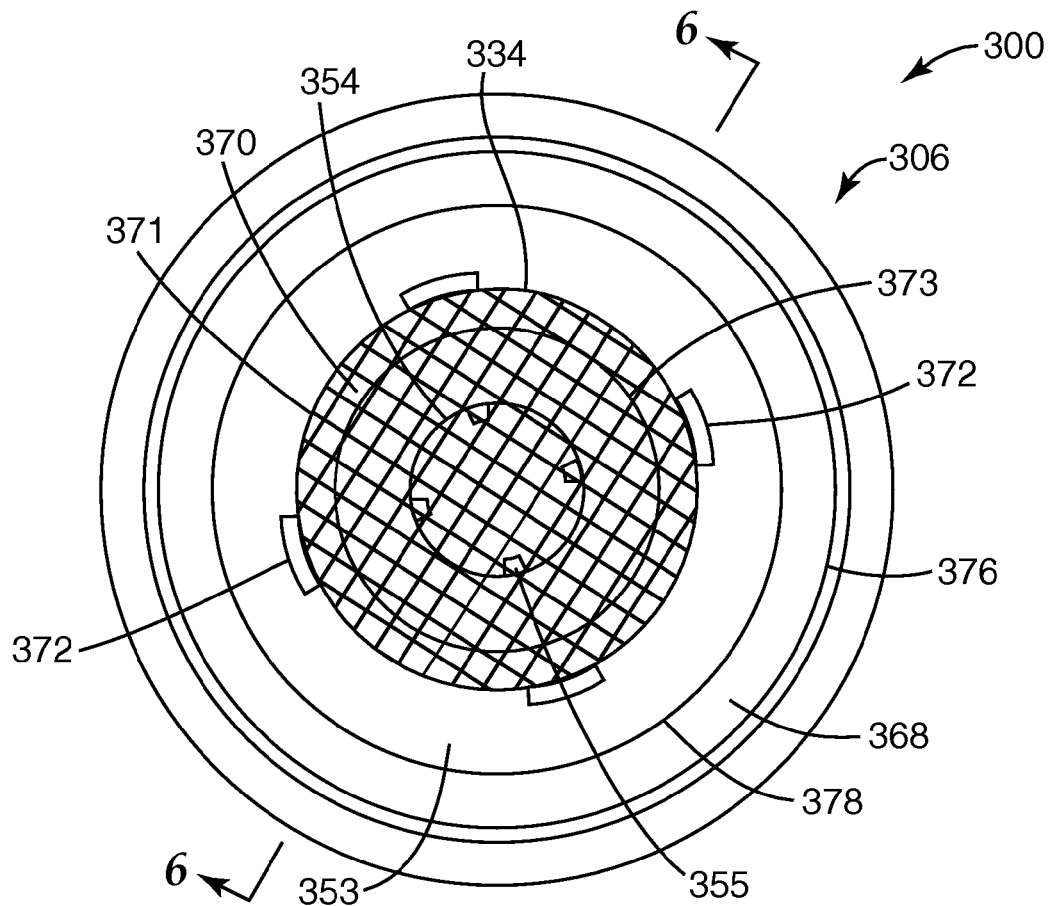
FIG. 5 is a bottom view of a lid of a sample preparation system according to another embodiment of the present disclosure.
Figure 6:
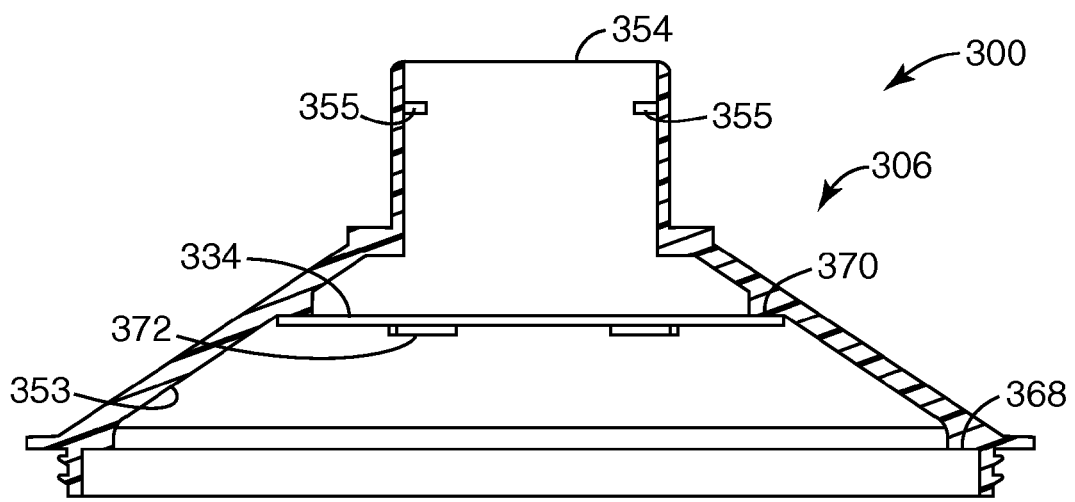
FIG. 6 is a cross-sectional view of the lid of FIG. 5, taken along line 6-6 in FIG. 5.
Figure 14:
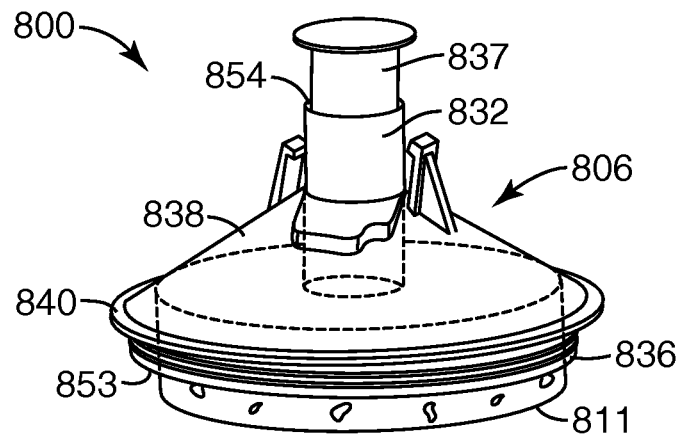
FIG. 14 is a perspective view of a sample preparation system according to another embodiment of the present disclosure.

As shown in FIG. 3, the inner surface 153 of the lid 106 can include a variety of inner circumferential edges to which other components (e.g., additional or alternative filters, the concept of which is illustrated in FIGS. 5-6 and described below) can be coupled. The inner circumferential edges can have any orientation desired, depending on what other components are desired to be coupled to the edges. In some embodiments, the inner circumferential edges are oriented substantially orthogonally to the central longitudinal axis of the lid 106, such that the edges are substantially horizontal in FIG. 3. In some embodiments, a substrate (not shown) can be coupled to the inner surface 153 of the lid 106. An example of this concept is illustrated in FIG. 14 and described below.

In addition, the lid 106 can include a variety of inwardly-extending members to which other components (e.g., filters) can be coupled. For example, as shown in FIG. 3, the filter 134 is supported by the frame 135, and the lid 106 includes inwardly-extending members 155 to which the frame 135 can be coupled via a variety of coupling means, including, but not limited to, any of the coupling means described above. The inwardly-extending members 155 can be integrally formed with the lid 106.

The filter 134 can be of any geometrical shape to sufficiently filter the liquid composition 114. In some embodiments, the filter 134 is deformable and/or collapsible (i.e., such that the filter 134 folds under its own weight). In some embodiments, the filter 134 is rigid and retains its shape (i.e., does not fold under its own weight). The size and number of filters 134 used in a sample preparation system 100, and porosity thereof, may vary, depending on the desired analyte(s), the type and size of insoluble matter in the source 112 or the loaded substrate 115, the size of the loaded substrate 115, and the level of breakdown of the loaded substrate 115.

By way of example only, in some embodiments, the liquid composition 114 comprises food, the desired analyte is bacteria, and the insoluble matter is food particles or debris. In such embodiments, for example, the filter 134 can be selected to retain and/or separate the food particles, while allowing the bacteria of interest (if present) to pass through the filter 134 for subsequent analysis. By way of further example, in some embodiments, the liquid composition 114 comprises a lysed bacterial cell culture, the desired analyte is one or more of DNA, RNA, a protein, or a metabolite, and the insoluble matter is cellular debris. In such embodiments, for example, the filter 134 can be selected or treated (e.g., derivatized with biomolecule-binding agents, such as antibodies) to retain and/or separate the cellular debris, while allowing the desired DNA, RNA, protein, and/or metabolite to pass through the filter 134 for subsequent analysis. Alternatively, for example, the filter 134 can be selected or treated to retain the desired DNA, RNA, protein and/or metabolite, while allowing the cellular debris to pass through the filter 134.

The filter 134 can have a variety of pore sizes sufficient for retaining particles from the liquid composition 114, while allowing the desired analyte(s) (if present) in the liquid composition 114 to pass through the filter 134 for extraction and/or sampling. Alternatively, the filter 134 can be sized, charged and/or functionalized to retain the desired analyte(s), while allowing undesired material to pass through the filter 134. In such embodiments, the sample can include at least a portion of the filter 134, which can be further processed (e.g., enriched, concentrated, analyzed, etc.).

In some embodiments, the filter 134 has an average pore or mesh size of at least 2 µm, in some embodiments, at least 5 µm, in some embodiments, at least 40 µm, in some embodiments, at least 80 µm, and in some embodiments, at least 120 µm. In some embodiments, the filter 134 has an average pore or mesh size of at most 2000 µm, in some embodiments, at most 1000 µm, in some embodiments, at most 500 µm, in some embodiments, at most 200 µm, in some embodiments, at most 50 µm, in some embodiments, at most 10 µm and in some embodiments, at most 1 µm (e.g., if it is desired to restrict bacteria from passing through the filter 134).

In the embodiment illustrated in FIGS. 2 and 3, the filter 134 is located in the lid 106, generally in line with the central longitudinal axis of the lid 106. However, in some embodiments, the filter 134 is positioned in an "off-axis" position of the lid 106. For example, an aperture 158 is shown in dashed lines in FIG. 2 to represent a possible "off-axis" position for the filter 134 in the lid 106. An alternative or an additional port can be positioned at the location of the aperture 158 and coupled thereto. The filter 134 can be permanently or removably coupled at one or both locations.

In some embodiments, particularly embodiments that do not employ the liner 104, the filter 134 can alternatively, or additionally, access the interior of the sample preparation system 100 (i.e., the first reservoir 120 of the container 102) via an aperture 160 in the sidewall 129 of the container 102 or the aperture 124 in the base 127 of the container 102 (or an aperture formed in a different location of the base 127 of the container 102). In such embodiments, the filter 134 can be permanently or removably coupled to the sidewall 129 or the base 127 of the container 102. An alternative or additional port can be positioned at the location of the apertures 160 and 124 and coupled thereto. In some embodiments, the sample preparation system 100 can include more than one port, such as the port 132 in the lid 106, an additional port at the location of the aperture 158 in the lid 106, an additional port at the location of the aperture 160 in sidewall 129 of the container 102, and/or an additional port at the location of the aperture 124 in the base 127 of the container 102. The cover 109 or a similar closure device can be used to seal any of the ports at any location on the sample preparation system 100.

Because of the different locations possible for the filter 134, the filter 134 can be shaped and dimensioned to accommodate its position in the sample preparation system 100 and the particular application of use. In any of the possible locations for the filter 134, the filter 134 can be positioned wholly above or wholly below the level 165 of the liquid composition 114, or the filter 134 can be positioned partially above and partially below the level 165 of the liquid composition 114, depending on the type of filtering desired, and how the filter 134 is intended to filter the liquid composition 114. For example, in the embodiment illustrated in FIG. 2, the filter 134 is coupled to the port 132 and, depending on how high the level 165 of the liquid composition 114 is, would typically extend from the port 132 into the interior of the sample preparation system 100, such that the filter 134 is positioned partially above and partially below the level 165 of the liquid composition 114.

The filter 134 is in fluid communication with the interior of the liner 104 and the liquid composition 114 and acts to filter the liquid composition 114 to form a filtrate 116. The filtrate 116 is disposed within the volume of the filter 134 and can be extracted and/or sampled from the adjacent port 132. In embodiments employing filters 134 at multiple locations, the filtrate 116 can be sampled from any of the ports or apertures described above.

The filter 134 can be formed from a variety of materials, including, but not limited to one or more of nylon, fluorinated polymers (e.g., polytetrafluoroethylene (PTFE)), cellulosics (e.g., modified celluloses such as cellulose acetate and nitrocellulose), fiberglass, papers, and combinations thereof. In some embodiments, the filter 134 can be formed of a woven web, a nonwoven web, a molded structure, a foam, fabric, a fibrous web, and combinations thereof. The surface area of the filter 134 can be increased by pleating the filter 134, or by other similar techniques. The thickness of the filter 134 can be controlled by calendering or felting processes.

In some embodiments (no matter which location the filter 134 is in), the filter 134 can be used as a retainer or holder of the loaded substrate 115. An example of this concept is illustrated in FIG. 4 and described below.

As mentioned above, the liner 104 can be disposable. In addition, in some embodiments, one or more of the lid 106, the cover 109 and the filter 134 can also be disposable. For example, in some embodiments, the lid 106 can be coupled to the liner 104, and the cover 109 and the filter 134 can be coupled to the lid 106. The liner 104, the lid 106, the filter 134 and the cover 109 can form a disposable portion of the sample preparation system 100 that can be used without contaminating the container 102 or the collar 108. The disposable portion can be removed from the container 102 and disposed. The container 102 and collar 108 can then be reused with a new liner 104, lid 106, filter 134 and cover 109.

Figure 4:
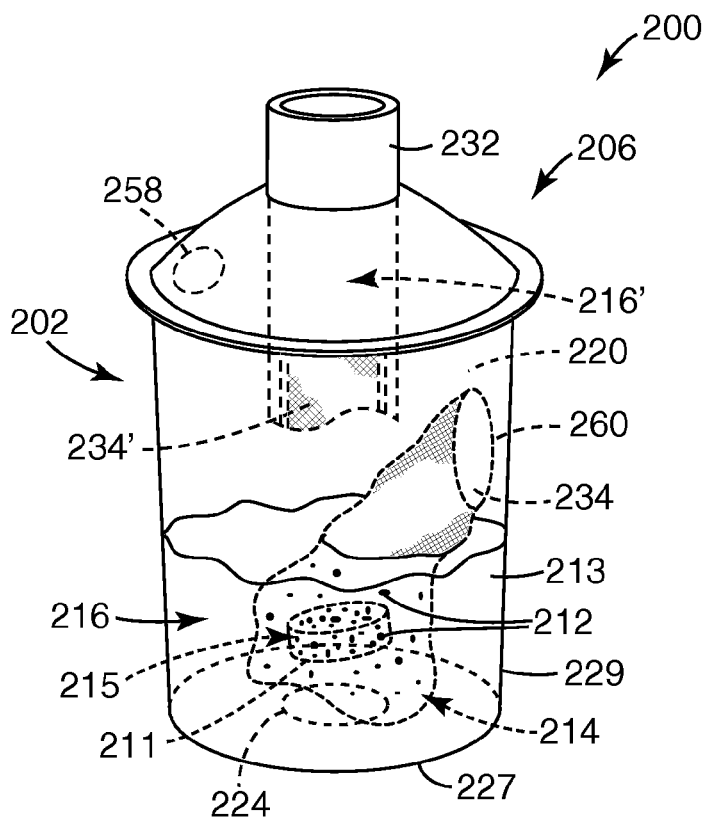
FIG. 4 is a perspective view of a sample preparation system according to another embodiment of the present disclosure.

FIG. 4 illustrates a sample preparation system 200 according to another embodiment of the present disclosure, wherein like numerals represent like elements. The sample preparation system 200 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 200 series. Reference is made to the description above accompanying FIGS. 2-3 for a more complete description of the features and elements (and alternatives to such features and elements) of the embodiment illustrated in FIG. 4.

The sample preparation system 200 includes a container 202 and a lid 206. The sample preparation system 200 does not include a liner, and the lid 206 is coupled directly to the container 202. The sample preparation system 200 further includes a filter 234 which is fluidly coupled to an aperture 260 formed in a sidewall 229 of the container 202. Unlike the filter 134 of the sample preparation system 100, the filter 234 functions as a retainer or holder for a loaded substrate 215 including a source 212 and a substrate 211, and a liquid composition 214 including the source 212 and a diluent 213.

The filter 234 is collapsible and sized to accommodate the size of the loaded substrate 215. In the embodiment illustrated in FIG. 4, the filter 234 is formed of a woven fabric (e.g., nylon), however, any of the above-described filter materials could be used instead. However, other types of filters (e.g., more rigid or of a different size) can be employed instead. The loaded substrate 215 shown in the embodiment illustrated in FIG. 4 is in the form of a sponge, which can be smooth or textured. However, the sponge is shown in FIG. 2 by way of example only, and it should be understood that the substrate 111 can be formed of any of the above-described materials and can be in any of the above-described forms without departing from the spirit and scope of the present disclosure.

The filter 234 can be permanently coupled to the container 202 and the loaded substrate 215 can be added to the filter 234, or the filter 234 can be removably coupled to the container 202, and the loaded substrate 215 can be added to the filter 234 prior to or after the filter 234 is coupled to the container 202. In some embodiments, the filter 234 can be free-floating within the first reservoir 220 of the container 202, such that the filter 234 contains the loaded substrate 215 and the diluent 213 is able to flow in and out of the interior of the filter 234 to interact with the loaded substrate 215.

The loaded substrate 215 is positioned within the filter 234, and the filter 234 is positioned at least partially below the level of the diluent 213 in the container 202 and is in fluid communication with the interior of the container 202, such that the source 212 from the loaded substrate 215 can be combined with the diluent 213 to form a liquid composition 214 within the filter 234. The liquid composition 214 positioned within the filter 234 includes the analyte(s) of interest (if present) in the diluent 213, as well as any other soluble or insoluble matter from the source 212. During agitation, the loaded substrate 215 and the diluent 213 can be mixed to allow the source 212 to be dissolved, dispersed, suspended and/or emulsified in the diluent 213. The pore size of the filter 234 will be adapted such that the diluent 213 and any analyte(s) of interest (if present) in the diluent 213 are free to flow in and out of the filter 234, such that the resulting filtrate 216 is positioned outside of the filter 234 and within the reservoir 220 of the container 202, and includes the diluent 213 and any present analyte(s) of interest.

The filtrate 216 can be sampled from any of a variety of ports or apertures, including the port 232 in the lid 206, the aperture 258 in the lid 206, an additional aperture in the sidewall 229 of the container 202, and/or an aperture 224 in the base 227 of the container 202. In addition, instead of being coupled to the sample preparation system 200 via the aperture 260, the filter 234 can instead be coupled to the sample preparation system 200 via any of a variety of ports or apertures, including the port 232 in the lid 206, the aperture 258 in the lid 206, and/or an aperture 224 in the base 227 of the container 202. In some embodiments, as shown in FIG. 4, one or more of the ports can include an additional filter 234' that functions in the same way as the filter 134 of the sample preparation system 100. In such embodiments, the filtrate 216 can be further filtered by the filter 234', and the resulting filtrate 216' is disposed within the filter 234' and can be extracted and/or sampled from the adjacent port (i.e., port 232 in FIG. 4).

The sample preparation system 200 can further include a liner, in which case the diluent 213 and resulting filtrate 216 can be positioned within the liner, provided that sufficient sealing is provided between the liner and the container 202 at the location of the aperture 260.

FIGS. 5-6 illustrate a sample preparation system 300 according to another embodiment of the present disclosure, wherein like numerals represent like elements. The sample preparation system 300 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 300 series. Reference is made to the description above accompanying FIGS. 2-3 for a more complete description of the features and elements (and alternatives to such features and elements) of the embodiment illustrated in FIGS. 5-6.

FIGS. 5-6 show only the lid 306 of the sample preparation system 300. The other components of the sample preparation system 300 can be assumed to include any of the other respective components of the sample preparation systems described above and illustrated in FIGS. 2-4, and thus for simplicity, are not shown in FIGS. 5-6.

The lid 306 is substantially similar to the lid 106 described above and illustrated in FIGS. 2-3, except that the lid 306 includes a filter 334 that is substantially planar and coupled to the inner surface 353 of the lid 306. The inner surface 353 of the lid 306 includes an upper inner circumferential edge 370 and a lower inner circumferential edge 368. As shown in FIG. 5, the upper inner circumferential edge 370 includes a downwardly facing surface that extends from an outer circumference 371 to an inner circumference 373. Similarly, the lower inner circumferential edge 368 includes a downwardly facing surface that extends from an outer circumference 376 to an inner circumference 378. The outer periphery of the filter 334 is coupled to the upper inner circumferential edge 370 of the inner surface 353. In addition, the filter 334 is in contact with retaining walls 372. The retaining walls 372 extend downwardly from the inner surface 353 of the lid 106 to retain the outer periphery of the filter 334.

The filter 334 can be coupled to the lid 306 using the same coupling means described above with respect to the lid 106. The filter 334 can be permanently or removably coupled to the lid 306. The degree of coupling between the filter 334 and the lid 306 may vary depending on a number of factors including, but not limited to, the filter 334 material, the lid 306 material, the size and texture of the coupled surface area, and the type of coupling means used. For example, if the filter 334 includes frayed edges, a wider and/or knurled coupling surface area may be used (e.g., the upper inner circumferential edge 370 can be knurled). Such a wider and/or knurled ultrasonic weld may capture frayed edges of the filter 334. To minimize the amount of fraying, the filter 334 can be cut using a laser, which can fuse the edges of the filter 334. Because the resulting laser-cut filter 334 would include a minimum amount of fraying, if any, a narrower coupling area can be used. In some embodiments, the coupling area extends completely around the outer periphery of the filter 334. In some embodiments, the coupling area can have an average width (i.e., a dimension within the same plane and substantially perpendicular to the outer periphery of the filter 334) of up to 5.0 mm, and in some embodiments, ranging from 1.0 mm to 3.0 mm. Alternatively, the filter 334 can be integrally formed with the lid 306, for example, by a molding process.

The filter 334 can be formed of the same material as the lid 306 or a different material. The filter 334 may be flexible, or semi-rigid. In some embodiments, the filter 334 is formed from a nylon nonwoven or woven fabric, while the lid 306 is an injection molded part formed of a polymer, such as polypropylene. In such embodiments, the nylon filter 334 can be coupled to the lid 306 via an ultrasonic welding technique. During ultrasonic welding, at least a portion of the upper inner circumferential edge 370 can melt to mechanically bond the filter 334. Since nylon has a higher melting temperature than polypropylene, the nylon filter 334 can maintain its structural integrity during the ultrasonic welding process. In such embodiments, at least a portion of the upper inner circumferential edge 370 can enter into a portion of filter 334, thereby encapsulating a portion of the filter 334.

The filter 334 can have dimensions and shapes that vary for a given application. The filter 334 can have any desired shape including, but not limited to, a circular shape, a square shape, a rectangular shape, a triangular shape, a polygonal shape, a star shape, other suitable shapes, and combinations thereof. In the embodiment illustrated in FIGS. 5 and 6, the filter 334 has a substantially circular shape.

The dimensions of the filter 334 may vary depending on the size of the lid 306. In some embodiments, the filter 334 has a largest dimension (i.e., length, width, or diameter) ranging from 15 mm to 100 mm, although the filter 334 may have smaller or larger dimensions. For example, in some embodiments, the filter 334 can have a circular shape and a diameter of 56 mm.

With continued reference to FIGS. 5 and 6, the retaining walls 372 can be integrally formed with the lid 306. In some embodiments, as shown in FIG. 5, the lid 306 comprises two or more retaining walls 372, wherein (i) each retaining wall 372 has a circumferential length greater than its thickness, (ii) each retaining wall 372 is positioned along an outer periphery of the filter 334, and (iii) the total circumferential length of the two or more retaining walls 372 is less than the total circumferential length of the outer periphery of the filter 334.

As shown in FIG. 5, the lid 306 includes four retaining walls 372 equally spaced from one another along outer circumference 371 of the upper inner circumferential edge 370. In some embodiments, each retaining wall 372 has a thickness ranging from 800 μm to 1200 μm, a length (i.e., in this exemplary embodiment, an arc length) extending a distance ranging from 1.0 mm to 22.0 mm along outer circumference 371, and a height ranging from 1.0 mm to 5.0 mm. In some embodiments, each retaining wall 372 has a segmented configuration so as to not inhibit (or to minimize the effect on) fluid flow around the retaining wall 372.

The lid 306 includes an opening 354 and inwardly-extending members 355. The inwardly-extending members 355 can be used to couple an additional filter (not shown) to the lid 306 in the same way that the filter 134 is coupled to the lid 106 in FIGS. 2 and 3. In such embodiments, the filter 334 is located below the additional filter, and the additional filter can have a length dimension less than the distance from the top the lid 306 to the filter 334.

In some embodiments, as shown in FIGS. 5 and 6, the filter 334 has a total surface area that is greater than a smallest cross-sectional area of the lid 306. In the lid 306, the smallest cross-sectional area is the cross-sectional area of lid opening 354. In some embodiments, more than one filter is coupled to the lid 306 in a similar manner as the filter 334. For example, in some embodiments, the filter 334 or an additional filter (not shown) can be coupled to the lower inner circumferential edge 368. That is, one or more filters 334 can be coupled to the lid 306 and positioned anywhere along the inner surface 353 of the lid 306. In embodiments employing more than one filter 334, the filters 334 can be similar to one another or different from one another. That is, the filters 334 can be formed of the same or different materials, and the filters 334 can have the same or sequentially smaller pore sizes.

As an example, a first filter 334 can be coupled to the upper inner circumferential edge 370 and can have a diameter of 56 mm, an element pore size of 80 μm, and can be at least partially surrounded by one or more retaining walls 372, while a second filter 334 can be coupled to the lower inner circumferential edge 368 and can have a diameter of 96 mm, an element pore size of 200 μm, and can be at least partially surrounded by the inner surface 353 of the lid 306.

Any of the above-described filters 134, 234 and 334 can be used in combination with one another in one sample preparation system. For example, as described above, the filter 134 can be used in combination with the filter 234 and/or the filter 334, to provide a series of filters for different applications, and/or for the removal of successively smaller particulates from the liquid composition.

Alternatively, or in addition, more than one of each type of filter 134, 234 or 334 can be employed (and in some embodiments, can be nested) for the removal of successively smaller particulates from the liquid composition. For example, the filters may be arranged where a coarse filter acts as a pre-filter with a larger pore size relative to subsequent filters, which have successively smaller pore sizes for the collection of a filtrate. The filters may be arranged for use of the sample preparation system in an upright position, and/or the filters may be arranged for use of the sample preparation system when it is tipped or inverted.

FIG. 7 illustrates a sample preparation system 400 according to another embodiment of the present disclosure, wherein like numerals represent like elements. The sample preparation system 400 shares many of the same elements and features described above with reference to the illustrated embodiments of FIGS. 2-3 and 5-6. Accordingly, elements and features corresponding to elements and features in the illustrated embodiment of FIGS. 2-3 and 5-6 are provided with the same reference numerals in the 400 series. Reference is made to the description above accompanying FIGS. 2-3 and 5-6 for a more complete description of the features and elements (and alternatives to such features and elements) of the embodiment illustrated in FIG. 7.

The sample preparation system 400 includes a container 402 having a first reservoir 420, a liner 404 having a second reservoir 422 and dimensioned to be received in the first reservoir 420 of the container 402, a lid 406, a collar 408, and a plunger 437. The lid 406 is similar to that of lids 106, 206 and 306 described above and illustrated in FIGS. 2-6, but further includes two upwardly-extending projections 439, which allow the sample preparation system 400 to be coupled to other devices, or provide coupling means for a cover (not shown). The lid 406 includes a port 432, which includes a plurality of ridges 441 that can provide alternative or additional coupling means for coupling the sample preparation system 400 to a cover or other devices. The lid 406 further includes a filter 434 that is substantially similar to the filter 334 shown in FIGS. 5-6 and described above.

As shown in FIG. 7, a loaded substrate 415 comprising a substrate 411 and a source 412 is positioned in the second reservoir 422 of the liner 404 and allowed to mix with a diluent 413 to form a liquid composition 414 that includes the source 412 and the diluent 413. In the embodiment illustrated in FIG. 7, the substrate 411 is in the form of a sponge.

In some embodiments, as shown in FIG. 7, the plunger 437 is configured to apply positive pressure to the exterior of the liner 404 when the plunger 437 is moved in a first direction $D_1$ toward the top of the container 402. As shown in FIG. 7, when the plunger 437 is used to apply pressure to the exterior of the liner 404, the liner 404 is compressed, the volume in the second reservoir 422 is reduced, and the liquid composition 414 is forced through the filter 434 to form a filtrate 416 that collects inside the lid 406 (e.g., when the sample preparation system 400 is inverted as shown in FIG. 7). The filtrate 416 can then be moved out of the sample preparation system 400 via the port 432.

The plunger 437 can be pressed in the direction $D_1$ to a position above the loaded substrate 415 such that the liner 404 (e.g., a base 426 of the liner 404) does not contact the loaded substrate 415, or to a position where the loaded substrate 415 is at least partially compressed by the plunger 437 (and the liner 404), for example, to enhance the removal of the source 412 from the loaded substrate 415.

In some embodiments, the plunger 437 is configured to apply negative pressure to the interior of the liner 404. For example, in some embodiments, the plunger 437 is coupled to the liner 404, such that when the plunger 437 is moved in a second direction $D_2$ opposite the first direction $D_1$, toward the bottom of the container 402, the liner 404 expands, which creates a reduced pressure in its interior (i.e., the second reservoir 422), and which establishes a pressure differential between the second reservoir 422 and the exterior of the sample preparation system 400. This pressure differential can cause fluid to move into the second reservoir 422 via the port 432, for example.

In some embodiments, as shown in FIG. 7, the plunger 437 can include a handle 443 that is dimensioned to be received in an aperture 424 of the base 427 of the container 402. In some embodiments, the handle 443 of the plunger 437 can be sized more closely to the size of the aperture 424, and/or a sealing means (e.g., an o-ring) can be positioned between the handle 443 and the aperture 424 to form a seal. In the embodiment illustrated in FIG. 7, the handle 443 has a smaller diameter than the portion of the plunger 437 that contacts the liner 404 (e.g., the base 426 of the liner 404). The portion of the plunger 437 that contacts the liner 404 is dimensioned to be received in the first reservoir 420 of the container 402. However, in some embodiments, the plunger 437 has a uniform cross-section or a gradually decreasing cross-section (e.g., in the second direction $D_2$), and the aperture 424 in the container 402 is sized accordingly. The plunger 437 shown in FIG. 7 is shown by way of example only, but one of ordinary skill in the art should understand that a variety of shapes and sizes of plungers can be used without departing from the spirit and scope of the present disclosure. As a result of the plunger 437 cooperating with the exterior of the liner 404 to create a pressure differential, the plunger 437 can be used without contacting the liquid composition 414 and can be reused without risk of contamination.

The plunger 437 can be formed of a variety of materials, including the materials listed above with respect to the container 102, and the plunger 437 can be solid or hollow. The plunger 437 can be translucent (or even transparent), or opaque, depending on the application of use.

FIG. 8 illustrates a sample preparation system 500 according to another embodiment of the present disclosure, wherein like numerals represent like elements. The sample preparation system 500 shares many of the same elements and features described above with reference to the illustrated embodiments of FIGS. 2-3 and 5-7. Accordingly, elements and features corresponding to elements and features in the illustrated embodiments of FIGS. 2-3 and 5-7 are provided with the same reference numerals in the 500 series. Reference is made to the description above accompanying FIGS. 2-3 and 5-7 for a more complete description of the features and elements (and alternatives to such features and elements) of the embodiment illustrated in FIG. 8.

As shown in FIG. 8, the sample preparation system 500 includes a container 502 that includes a first reservoir 520, a liner 504 dimensioned to be received in the first reservoir 520 and including a second reservoir 522, and a lid 506. A collar (not shown) can also be employed to further secure the components of the sample preparation system 500 together. The second reservoir 522 is adapted to contain a loaded substrate 515 comprising a substrate 511 and a source 512 and a liquid composition 514 comprising the source 512 and a diluent 513. The sample preparation system 500 further includes a plunger 537 coupled to a filter 534. The filter 534 is adapted to filter the liquid composition 514 to form a filtrate 516 that comprises the analyte of interest (if present). In the embodiment illustrated in FIG. 8, the substrate 511 is in the form of a sponge.

The container 502 includes a base 527, a sidewall 529, and an aperture 524 defined in the base 527. The liner 504 includes a sidewall 528 and a base 526 that can be accessed, for example, via the aperture 524 in the base 527 of the container 502. The lid 506 includes a port 532 that defines an opening 554 in the lid 506 and the sample preparation system 500. The plunger 537 includes a handle 543 that is dimensioned to be received in the port 532, such that the handle 543 can be accessed from outside of the sample preparation system 500 to force the filter 534 through the liquid composition 514. In some embodiments, the handle 543 of the plunger 537 can be sized more closely to the size of the opening 554, and/or a sealing means (e.g., an o-ring) can be positioned between the handle 543 and opening 554 to form a seal. The lid 506 further includes an off-axis aperture 558 defined in a second port of the lid 506, which can serve, for example, as a degassing outlet to allow for the release of pressure from within the sample preparation system 500.

In some embodiments, as shown in FIG. 8, the filter 534 can be dimensioned to fit within the second reservoir 522 of the liner 504. In such embodiments, the filter 534 can form a seal with the sidewall 528 of the liner 504 by virtue of the deformability of the liner 504 and does not necessarily require additional sealing means between the outer surface of the filter 534 and the inner surface of the sidewall 528 of the liner 504. The deformability of the liner 504 can also allow for wider tolerances, such that the filter 534 does not have to be sized within a narrow range to still be able to cooperate with the liner 504.

Alternatively, in some embodiments, the sample preparation system 500 does not include a liner 504, and the filter 534 can be configured to cooperate with the container 502. For example, the filter 534 can be sized to fit within the first reservoir 520 of the container 502. In some embodiments, the sample preparation system 500 can include sealing means (e.g., an o-ring) positioned between the filter 534 and the sidewall 529 of the container 502. In some embodiments, the sidewall 529 of the container 502 is straight up and down (i.e., perpendicular to the base 527) to facilitate sealing the filter 534 with the sidewall 529. In some embodiments, the filter 534 includes an outer deformable (e.g., elastomeric) flange to allow the filter 534 to accommodate a taper in the sidewall 529 of the container 502. Such a flange could also be incorporated into embodiments employing the filter 504.

As the plunger 537 is pressed downwardly along a direction $D_1$, the filter 534 moves downwardly through the liquid composition 514, such that relatively large insoluble matter (i.e., any particulates having a size greater than the pore size of the filter 534) are maintained below the filter 534, and any soluble matter and relatively small insoluble matter (i.e., any particulates having a size less than the pore size of the filter 534) pass through the filter, such that the filtrate 516 is formed above the filter 534 in the second reservoir 522. The plunger 537 can be pressed in the direction $D_1$ to a set position above the loaded substrate 515 such that the filter 534 does not contact the loaded substrate 515 (e.g., the liner 504, the filter 534 and/or the plunger 537 can include one or more stops, the plunger 537 can be sized to only accommodate a certain depth in the second reservoir 522, etc.), or to a position where the loaded substrate 515 is at least partially compressed by the filter 534, for example, to enhance the removal of the source 512 from the loaded substrate 515.

In some embodiments, the handle 543 of the plunger 537 can be hollow and in fluid communication with the second reservoir 522. In such embodiments, at least a portion of the filtrate 516 can be received in the interior of the handle 543 of the plunger 537 and can be removed from the sample preparation system 500 via the handle 543. In such embodiments, the plunger 537 can include a cover dimensioned to receive the upper end of the handle 543. Alternatively, the plunger 537 can be hollow and not covered at its base by the filter 534, such that at least a portion of the liquid composition 514 and/or the loaded substrate 515 can be received in the interior of the handle 543 of the plunger 537. Such embodiments can allow the liquid composition 514 and/or the loaded substrate 515 to take up less space in the bottom of the second reservoir 522 and can allow the filter 534 to be moved further down in the second reservoir 522 along the direction $D_1$.

FIGS. 9-12 illustrate a sample preparation system 600 according to another embodiment of the present disclosure, wherein like numerals represent like elements. The sample preparation system 600 shares many of the same elements and features described above with reference to the illustrated embodiment of FIGS. 2-3. Accordingly, elements and features corresponding to elements and features in the illustrated embodiment of FIGS. 2-3 are provided with the same reference numerals in the 600 series. Reference is made to the description above accompanying FIGS. 2-3 for a more complete description of the features and elements (and alternatives to such features and elements) of the embodiment illustrated in FIGS. 9-12.

Figure 9:
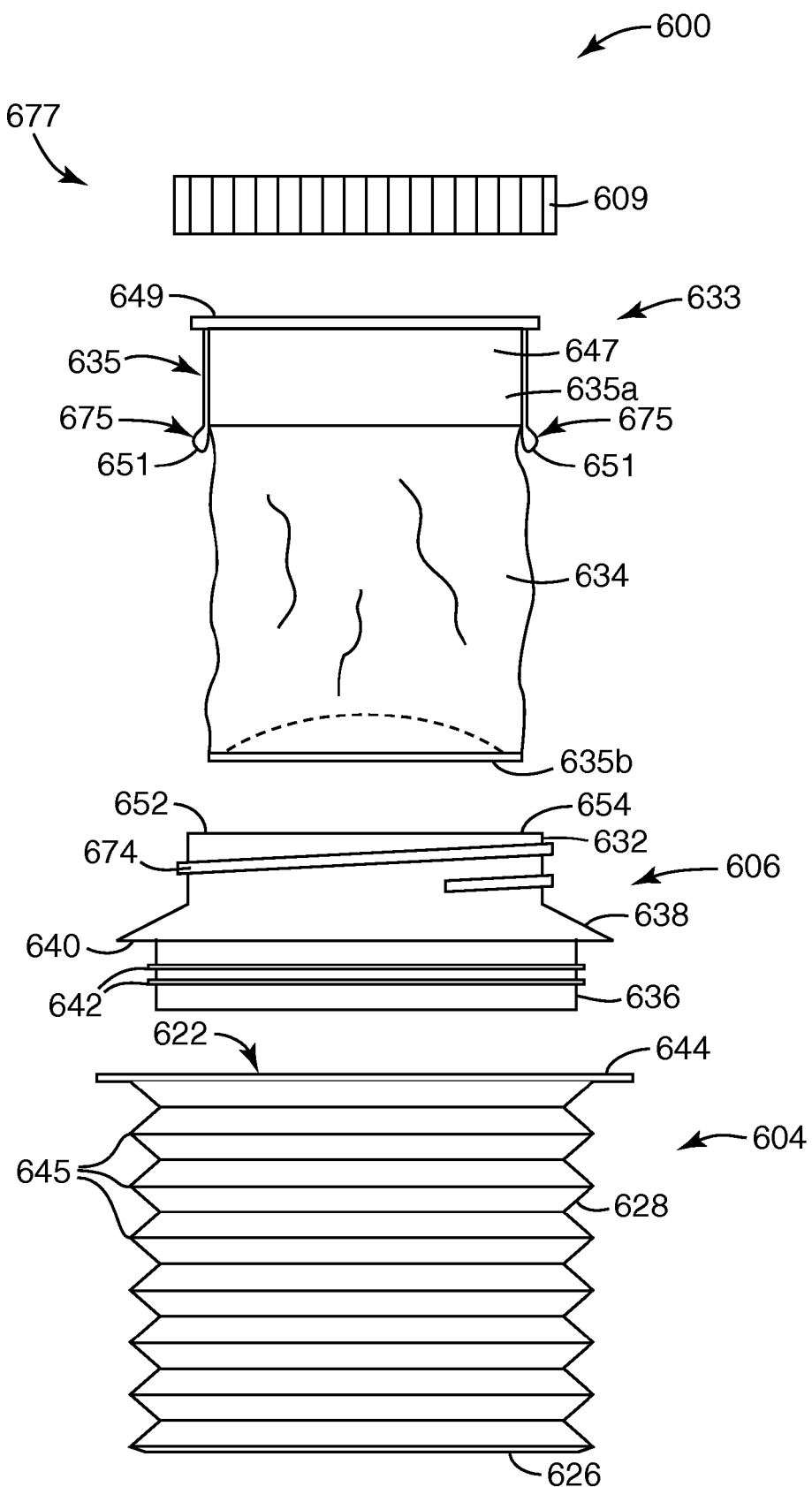
FIG. 9 is an exploded side view of a sample preparation system according to another embodiment of the present disclosure, the sample preparation system including a filter, and a lid assembly that includes a lid and a cover.

As shown in FIG. 9, the sample preparation system 600 includes a receptacle 604, a lid 606, a cover 609, and a filter assembly 633. The receptacle 604 is deformable, self-supporting and freestanding. The receptacle 604 includes a base 626 and a sidewall 628. The sidewall 628 includes an accordion-type configuration and includes a plurality of pleats or folds 645 to allow the sidewall 628 to be folded at each pleat 645 and to facilitate the collapse of the receptacle 604 substantially along its longitudinal axis, and particularly, to facilitate the collapse of the receptacle 604 substantially uniformly substantially along its longitudinal axis. In the embodiment illustrated in FIG. 9, the sidewall 628 includes a plurality of pleats or folds 645 by way of example only. However, it should be understood that the sidewall 628 can include other structures that would allow the sidewall 628 to collapse substantially uniformly substantially along its longitudinal axis, such as annular weakened portions in the sidewall 628 that are less rigid and/or less thick than the remainder of the sidewall 628 to allow the sidewall 628 to buckle at the locations of the annular weakened portions. Other suitable structures are also possible and within the spirit and scope of the present disclosure.

The base 626 of the receptacle 604 can be reinforced, made of a more rigid material, and/or made to be thicker relative to the sidewall 628 to encourage the receptacle 604 to collapse along its longitudinal axis. The receptacle 604 includes a reservoir 622 that is adapted to contain a loaded substrate and a liquid composition.

The receptacle 604 can be formed of a variety of materials, including the materials listed above with respect to the liner 104. The receptacle 604 can be translucent (or even transparent), or opaque, depending on the application of use. Any or all of the components of the sample preparation system 600 can be disposable (e.g., made for one-time use).

The lid 606 includes a port 632, which can be coupled to the filter assembly 633, a cylindrical portion 636 that is dimensioned to be received within the receptacle 604, and a generally conical (e.g., frusto-conical) portion 638 that extends from the cylindrical portion 636 to the port 632. At the junction between the cylindrical portion 636 and the conical portion 638, the lid 106 further includes a lip 640 that extends radially outwardly from the cylindrical portion 636 and the conical portion 638. The port 632 of the lid 606 is generally cylindrical and tubular in shape, such that the port 632 includes an inner surface 652 and defines an opening 654 in the lid 606, and in the sample preparation system 600, when assembled.

The cylindrical portion 636 of the lid 606 includes a plurality of circumferential outwardly-projecting protrusions 642 to allow the cylindrical portion 636 to be snap-fit or press-fit to the inner surface of the receptacle 604. The receptacle 604 can include an upper surface 644 that can form an abutting relationship with the lip 640 of the lid 606. The lid 606 and the receptacle 604 can be coupled together using any of the above removable or permanent coupling means in order to form a seal (e.g., a liquid-tight seal, a hermetic seal, or a combination thereof), such that the sample preparation system 600 is inhibited from leaking during normal operation. For example, the plurality of circumferential outwardly-projecting protrusions 642 can be ultrasonically-welded to the inner surface of the receptacle 604.

The filter assembly 633 includes a frame 635 and a filter 634. The frame 635 includes an upper portion 635a and a lower portion 635b, and the filter 634 is coupled therebetween. The upper portion 635a of the frame 635 is shaped and dimensioned to be coupled to the port 632 of the lid 606 and received within the port 632 of the lid 606 and the reservoir 622 of the receptacle 604. The frame 635 need not include the lower portion 635b, but the lower portion 635b gives the filter 634 additional weight and aids in exposing the filter 634 to the liquid composition in the reservoir 622 of the receptacle 604.

The upper portion 635a includes a tubular body 647 dimensioned to be received in the port 632 of the lid 606, a lip 649 coupled to the upper end of the tubular body 647 dimensioned to sit atop the port 632 of the lid 606, and a plurality of ribs 651. The ribs 651 are circumferentially-spaced about the tubular body 647. The embodiment illustrated in FIG. 9 includes two ribs 651, but as few or as many as necessary can be used. The ribs 651 are shaped to be coupled to the lid 606 in a snap-fit engagement. Particularly, the ribs 651 each include a cam surface 675 adapted to slide along the inner surface 652 of the port 632 as the upper portion 635a of the frame is moved into the port 632. In addition, the cam surface 675 of each rib 651 causes the respective rib 651 to be forced radially inwardly as the tubular body 647 is moved into the port 632, and further allows the respective rib 651 to snap (e.g., radially outwardly) into position under the bottom of the port 632 (i.e., on the inside of the lid 606).

The filter assembly 633 can then be removed from the lid 606 by pulling upwardly on the lip 649 of the frame 635 with sufficient force to move at least one rib 651 inwardly far enough to bring its cam surface 675 into contact with the inner surface 652 of the port 632, and to continue sliding the cam surface 675 upwardly along the inner surface 652 until the rib 651 is released from contact with the inner surface 652 of the port 632. Alternatively, the filter assembly 633 can be removed from the lid 606 by moving at least one rib 651 radially inwardly while applying an upward force to bring the cam surface 675 of the respective rib 651 into contact with the inner surface 652 of the port 632, or by squeezing the ribs 651 toward one another (e.g., radially inwardly) and moving the upper portion 635a of the frame 635 upwardly out of the port 632.

The filter 634 illustrated in FIG. 9 is collapsible and can be caused to hang downwardly in the reservoir 622 of the receptacle 604 at least partially by the weight of the lower portion 635b of the frame 635.

The cover 609 is shaped and dimensioned to receive at least a portion of the port 632. As a result, the cover 609 can be coupled to the port 632 of the lid 606 to close the opening 654 in the lid 606 and to seal (e.g., hermetically seal) the sample preparation system 600 from ambience. The cover 609 can be coupled to the lid 106 using any of the above-described coupling means. In the embodiment illustrated in FIG. 9, the port 632 of the lid 606 includes a plurality of threads 674 adapted to matingly engage with threads (not shown) on the inside of the cover 609, such that the cover 609 can be screwed onto the port 632. However, any of the other coupling means described above can be employed to couple the cover 609 to the lid 606 to close the opening 654 in the lid 606. The cover 609 and the lid 606 can together form a lid assembly 677, and the lip 649 of the filter assembly 633 can be sandwiched between the cover 609 and the upper end of the port 632 of the lid 606 when the sample preparation system 600 is assembled and closed.

Figure 10:
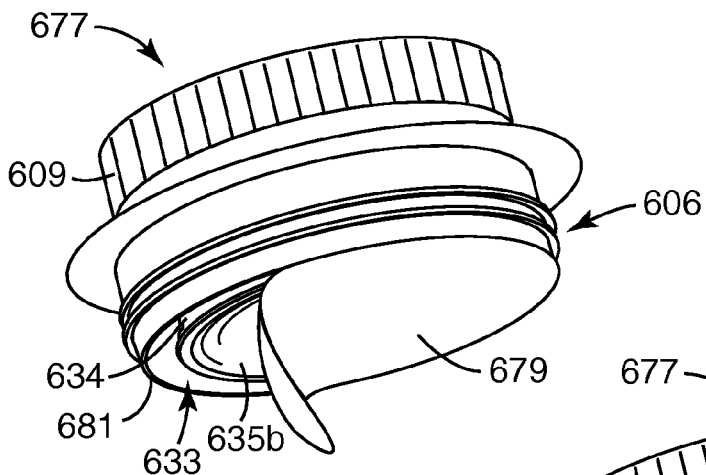
FIG. 10 is a perspective view of the lid assembly and filter of FIG. 9, with the filter in a compressed state.
Figure 11:
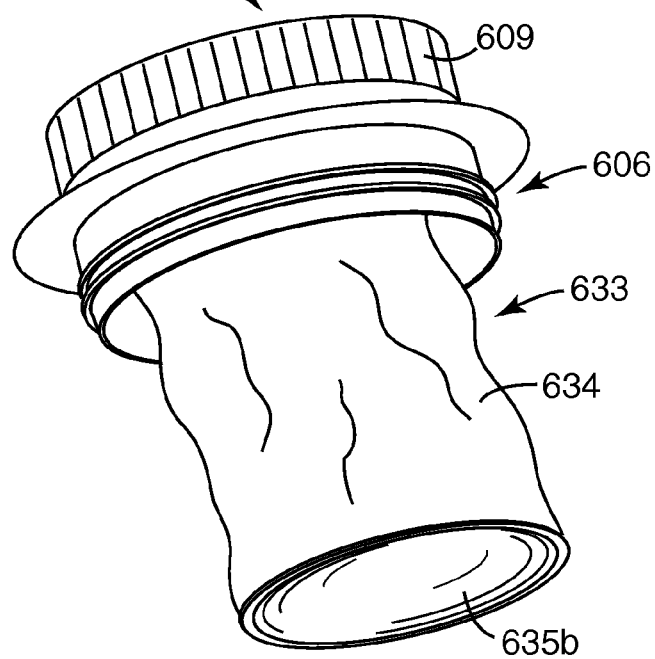
FIG. 11 is a perspective view of the lid assembly and filter of FIGS. 9 and 10, with the filter in an uncompressed state.

FIG. 10 illustrates the lid assembly 677 and the filter assembly 633 with the cover 609 coupled to the lid 606, and the filter assembly 633 coupled therebetween. The filter 634 is shown in a compressed state, such that the filter assembly 633 is contained in the interior of the lid 606. The lower portion 635b of the filter frame 635 is rigid relative to the collapsible filter 634, which aids in collapsing the filter 634 along its longitudinal axis, such that the filter 634 can be compressed into the interior of the lid 606 by pressing upwardly on the lower portion 635b of the frame 635. A removable barrier film 679 can be coupled to a lower surface 681 of the lid 606 to maintain the filter 634 in a compressed state within the interior of the lid 606. The lid assembly 677 can be sterilized and packaged with the filter 634 in its compressed state and the filter assembly 633 contained inside the lid 606 by the removable barrier film 679. A user can then remove the removable barrier film 679 prior to use (e.g., in a sterile environment) to allow the filter 634 (and the lower portion 635b of the frame 635, if employed) to hang below the lid assembly 677 in an uncompressed state. The removable barrier film 679 can also be removed just prior to coupling the lid 606 to the receptacle 604 to allow the filter 634 to drop into the reservoir 622 of the receptacle 604. The uncompressed state of the filter 634 following removal of the removable barrier film 679 is shown in FIG. 11.

The removable barrier film 679 can be coupled to the lid 606 using any of the coupling means described above, and can be formed of a variety of materials, including, but not limited to, a polyolefin, including, but not limited to polypropylene (e.g., low density polyethylene (LDPE)), polyethylene; poly (methylpentene); polyamide (e.g., NYLON®); compressed blown microfiber (cBMF); urethane; polyester; polycarbonate; and combinations thereof. In some embodiments, the removable barrier film 679 can include, for example, a heat sealed "strippable" film, such as a 3M™ SCOTCHPAK™ release liner (3M Company, St. Paul, Minn.). The removable barrier film 679 can be translucent (or even transparent), or opaque. The removable barrier film 679 can be formed by a variety of processes, including, but not limited to a molding process, extrusion, a blow film forming process, etc., and combinations thereof.

Figure 12:
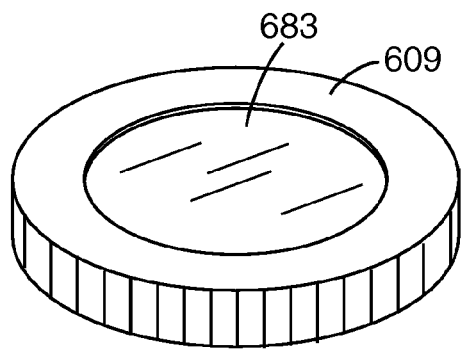
FIG. 12 is a top perspective view of the cover of FIGS. 9-11.

In some embodiments, as shown in FIG. 12, the cover 609 includes a frangible barrier 683 which can be punctured to access either the reservoir 622 of the receptacle 604, or the volume within the filter 634. The barrier 683 can include a membrane, a non-porous film, and combinations thereof. In addition, the frangible barrier 683 can be formed of a variety of materials that allow the barrier 683 to be frangible (e.g., punctured by a pipette tip), including, but not limited to, a polyolefin, including, but not limited to polypropylene (e.g., low density polyethylene (LDPE)), polyethylene; poly(methylpentene); polyamide (e.g., NYLON®); compressed blown microfiber (cBMF); urethane; polyester; polycarbonate; synthetic or natural elastomers; 3M™ TEGADERM™ film dressing (3M Company, St. Paul, Minn.), and combinations thereof. In some embodiments, the barrier 683 is instead formed over the opening 654 in the lid 606. In such embodiments, the cover 609 can be solid and can be used to cover the lid 606, for example, after the barrier 683 has been punctured, or the cover 609 can include an additional barrier. Alternatively, in embodiments in which the barrier 683 is formed over the opening 654 in the lid 606, a cover 609 need not be employed. Whether employed with the lid 606 or the cover 609, or both, or another portion of the sample preparation system 600, the barrier 683 can include the additional functionality of being gas-permeable to allow for gas exchange between the interior of the reservoir 622 and ambience (e.g., to provide oxygen to aerobic bacteria of interest).

Figure 13:
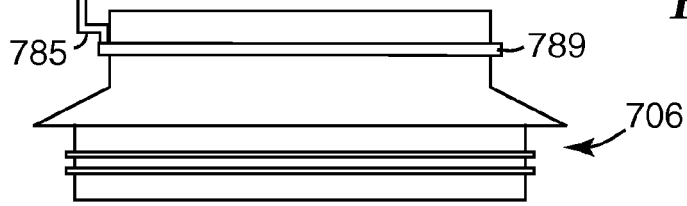
FIG. 13 is a side view of a lid assembly of a sample preparation system according to another embodiment of the present disclosure.

FIG. 13 illustrates a sample preparation system 700 according to another embodiment of the present disclosure. FIG. 13 shows only the lid assembly 777 of the sample preparation system 700. The other components of the sample preparation system 700 can be assumed to include any of the other respective components of the sample preparation systems described above and illustrated in FIGS. 2-12, and thus for simplicity, are not shown in FIG. 13.

The lid assembly 777 includes a lid 706 and a cover 709 coupled to the lid 706 via a hinge 785. In some embodiments, as shown in FIG. 13, the hinge 785 is a living hinge, and the cover 709 is integrally formed with the lid 706. In some embodiments, the hinge 785 is formed separately from one or both of the lid 706 and the cover 709. The cover 709 is a flip-top cover and can be coupled with the lid 706 via a snap-type engagement. In the embodiment illustrated in FIG. 13, the cover 709 includes a projection 787 that can be snapped onto a ridge 789 on the lid 706. The cover 709 can include other sealing means (e.g., an o-ring), such that when the cover 709 is closed over the lid 706, the cover 709 forms a seal (e.g., a liquid tight seal, a hermetic seal, etc.) with the lid 706.

FIG. 14 illustrates a sample preparation system 800 according to another embodiment of the present disclosure, wherein like numerals represent like elements. The sample preparation system 800 shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 800 series. Reference is made to the description above accompanying FIGS. 2-3 and 7 for a more complete description of the features and elements (and alternatives to such features and elements) of the embodiment illustrated in FIG. 14.

FIG. 14 shows only an upper portion of the sample preparation system 800. The other components of the sample preparation system 800 can be assumed to include any of the other respective components of the sample preparation systems described above and illustrated in FIGS. 2-13, and thus for simplicity, are not shown in FIG. 14.

The sample preparation system 800 includes a lid 806 and a substrate 811 coupled to the lid 806. The substrate 811 is coupled to an inner surface 853 of the lid 806 in such a way that the bottom of the substrate 811 extends below the bottom of the lid 806. The substrate 811 is illustrated in FIG. 14 as being in the form of a sponge.

The lid 806 includes a port 832 that defines an opening 854 in the lid 806 and the sample preparation system 800; a cylindrical portion 836 that allows the lid 806 to be coupled to a container and/or a liner; a conical (e.g., frusto-conical) portion 838 that extends from the cylindrical portion 836 to the port 832; a lip 840 formed at the junction of the cylindrical portion 836 and the conical portion 838 to aid in coupling the lid 806 to a container and/or a liner; and upwardly-extending projections 839 that can provide coupling means for a cover or another device.

In the embodiment illustrated in FIG. 14, the substrate 811 is coupled to the lid 806 in such a way as to extend below the bottom of the cylindrical portion 836 of the lid 806. By allowing the substrate 811 to extend below the lid 806, the substrate 811 is exposed both for collection of a source, and for combining with a diluent to form a liquid composition that includes the source and the diluent.

Any portion of the lid 806 can function as a handle to allow the substrate 811 to pick up a source from a surface of interest without contaminating a user's hands. Alternatively, any portion of the lid 806 could be coupled to another device (e.g., a robotic arm) that could be used to collect a source form a surface of interest (e.g., by moving the lid 806 along the surface).

The sample preparation system 800 further includes a plunger 837 that is coupled to the lid 806. At least a portion of the plunger 537 is dimensioned to be received in the port 832 and to extend into the interior of the lid 806 to contact the substrate 811. The plunger 837 is adapted to facilitate the removal of the substrate 811 from the lid 806. For example, the plunger 837 can be used to decouple the substrate 811 from the lid 806 and to drop the substrate 811 (e.g., after it has been loaded with a source) into the reservoir of a container and/or a liner. The plunger 837 can be depressed prior to, during, or subsequent to coupling the lid 806 to a container and/or a liner. The plunger 837 can include a variety of suitable shapes and sizes and can be formed of any of the variety of materials described above with respect to the plunger 437.

In some embodiments, the plunger 837 is not employed, and the substrate 811 can either remain coupled to the lid 806 during use of the sample preparation system 800, or the substrate 811 can become decoupled from the lid 806 during use of the sample preparation system 800. For example, the substrate 811 can become decoupled from the lid 806 during or after an agitation process, or after a diluent is allowed to be absorbed into the substrate 811, e.g., causing the substrate 811 to swell with the diluent.

The sample preparation system 800 can further include a filter (not shown) that can be adapted to filter the liquid composition to form a filtrate. In some embodiments, the filter can be substantially the same as the filter 134 illustrated in FIGS. 2-3, and the substrate 811 can include an aperture dimensioned to receive the filter to allow the filter to be positioned in fluid communication with the liquid composition when the lid 806 is coupled to a container and/or a liner.

In use, the lid 806 can be used to collect a source on the substrate 811 to form a loaded substrate. The lid 806 can then be coupled to a container and/or a liner such that the loaded substrate is positioned in fluid communication with a diluent. The loaded substrate can be dropped into the reservoir (e.g., into the diluent to either float in the diluent or settle to the bottom of the reservoir), or the loaded substrate can remain coupled to the lid 806, such that the loaded substrate does not contact any inner surface of a container or liner while positioned in the reservoir, but rather is spaced a distance from any such inner surface.

The diluent can be allowed to interact with the loaded substrate to form a liquid composition that includes the source and the diluent. The loaded substrate and the diluent can be agitated to enhance formation of the liquid composition. Furthermore, if the diluent includes enrichment media, at least one analyte of interest can be enriched. Such enrichment can occur, for example, by positioning the sample preparation system 800 in an incubation environment and/or by inverting the sample preparation system 800 to allow the diluent to remain in contact with the loaded substrate throughout the enrichment and/or incubation process. At least a portion of the liquid composition (or filtrate, if a filter is employed) can be removed from the sample preparation system 800 for concentration, further incubation, and/or analysis of an analyte of interest.

The substrate 811 is shown as being coupled to the lid 806 by way of example only. However, it should be understood that the substrate 811 can be coupled to any of the other components of the sample preparation system 800 instead. For example, the substrate 811 can be coupled to the internal side of a base of a container of the sample preparation system 800, or to the internal side of a sidewall of a container or a liner of the sample preparation system 800. In any of such embodiments, the substrate 811 can be loaded, for example, by using the component of the sample preparation system 800 to which the substrate 811 is coupled as a handle. In addition, positioning the loaded substrate in fluid communication with a diluent can be accomplished by coupling the respective component to another portion of the sample preparation system 800 or by assembling the sample preparation system 800.

Figure 15:
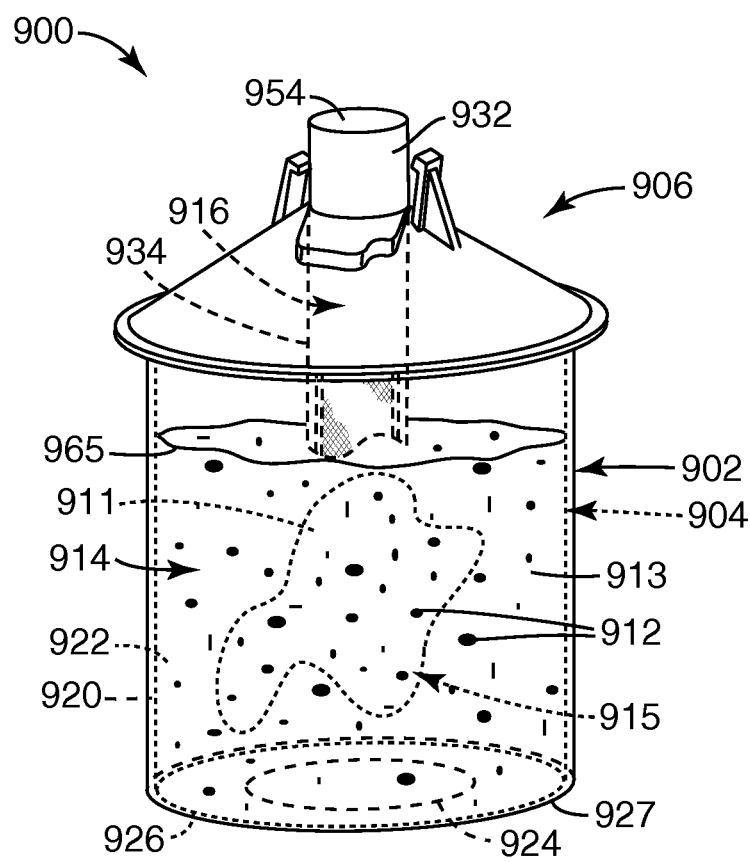
FIG. 15 is a perspective view of the sample preparation system according to another embodiment of the present disclosure.

FIG. 15 illustrates a sample preparation system 900 according to another embodiment of the present disclosure, wherein like numerals represent like elements. The sample preparation system 900 shares many of the same elements and features described above with reference to the illustrated embodiments of FIGS. 2-3 and 7. Accordingly, elements and features corresponding to elements and features in the illustrated embodiments of FIGS. 2-3 and 7 are provided with the same reference numerals in the 900 series. Reference is made to the description above accompanying FIGS. 2-3 and 7 for a more complete description of the features and elements (and alternatives to such features and elements) of the embodiment illustrated in FIG. 15.

The sample preparation system 900 includes a container 902 having a first reservoir 920, a liner 904 having a second reservoir 922 and dimensioned to be received in the first reservoir 920, a lid 906, and a filter 934. The lid 906 is substantially similar to the lid 406 shown in FIG. 7, and the filter 934 is substantially similar to the filter 134 shown in FIGS. 2-3. The filter 934 is adapted to form a filtrate 916. The lid 906 includes a port 932 that defines an opening 954 in the lid 906 and the sample preparation system 900.

As shown in FIG. 15, a loaded substrate 915 comprising a substrate 911 and a source 912 is positioned in the second reservoir 922 of the liner 904 and allowed to mix with a diluent 913 to form a liquid composition 914 that includes the source 912 and the diluent 913. In the embodiment illustrated in FIG. 7, the substrate 911 is in the form of a wipe.

The container 902 includes an aperture 924 formed in its base 927, which can allow access to the liner 904 (e.g., to a base 926 of the liner 904) to allow the liner 904 to be deformed. Such deformation of the liner 904 can be used to raise a level 965 of the liquid composition 914 to facilitate filtering of the liquid composition 914 or removal of the liquid composition 914 of the filtrate 916 from the sample preparation system 900. All or a portion (e.g., a sample) of the filtrate 916 can be removed from the interior of the filter 934. Particularly, a pressure differential can be established that causes the liner 904 to deform, to cause the liquid composition 914 to be forced through the filter 934, and to cause the filtrate 916 (or the liquid composition 914 when the filter 934 is not employed) to flow out of the sample preparation system 900. The pressure differential can be established by applying a positive pressure to the exterior of the liner 904 (e.g., to the base 926 of the liner 904 via the aperture 924 in the base 927 of the container 902) or by applying a negative pressure to the interior of the liner 904. As mentioned above, positive pressure can be applied to the liner 904 by hand or by another device, and can employ a manual or an automated process. Negative pressure (or a vacuum) can be applied to the interior of the liner 904, and particularly to the second reservoir 922 of the liner 904, for example, by coupling a vacuum source to the lid 906 (e.g., to the port 932 of the lid 906). A vacuum source can include, but is not limited to, a mechanical pump that creates a reduced pressure, or a manual pump (e.g., a syringe-plunger combination), and combinations thereof.

Any of the sample preparation systems 100, 200, 300, 400, 500, 600, 700, 800, and 900, and combinations thereof, can be used to prepare samples by generally following the sample preparation method 10 described above and illustrated in FIG. 1. One of ordinary skill in the art will also understand that various components from one sample preparation system described herein can be used in combination with other components from another sample preparation system described herein, without departing from the spirit and scope of the present disclosure. For example, the receptacle 604 can be used in place of the liner 904 in the sample preparation system 900. An exemplary method will now be described in detail using the sample preparation system 900 of FIG. 15.

The substrate 911 can be used to collect a source 912 from a surface to be tested to form a loaded substrate 915. The substrate 911 is a wipe and can therefore easily collect a source 912 from a relatively large surface of interest. The loaded substrate 915 and the diluent 913 can be added to the first reservoir 920 of the container 902 and combined (i.e., allowed to interact) to form a liquid composition 914 that includes the source 912 and the diluent 913. As mentioned above, the liner 904 or the container 902 can serve as a freestanding receptacle that can contain the liquid composition 914. Alternatively, the liner 904 can be deformable and self-supporting but not necessarily freestanding until the liner 904 is positioned in the container 902. The lid 906 can be coupled to the liner 904 prior to or after the liner 904 is positioned in the container 902. A collar (not shown) can be coupled to the container 902 to further secure the components of the sample preparation system 900 together, and the lid opening 954 can be closed using a cover (not shown).

The sample preparation system 900 can be agitated to allow the loaded substrate 915 to interact with the diluent 913, and to dissolve, disperse, suspend and/or emulsify the source 912 in the diluent 913. Agitation may include any of the above-described processes, and for example, can be linear, in a circular orbit, an elliptical orbit, a random orbit, a combination thereof, or of other means to ensure effective and efficient mixing of the loaded substrate 915 and the diluent 913. The sample preparation system 900 may be secured by clamping or other means during agitation to minimize spillage and/or loss of the liquid composition 914.

In some embodiments, the liquid composition 914 (or the contents of the sample preparation system 900) can be agitated by a Burell Model 75 Wrist Action Shaker (Burrell Scientific, Pittsburgh, Pa.), at a frequency of 10 to 2000 cycles/minute, and in some embodiments, at a frequency of 200 to 500 cycles/minute for a selected duration of time. In some embodiments, the sample preparation system 900 can be mounted at a distance from the shaker arm from between 5 cm and 50 cm, and in some embodiments, between 10 cm and 20 cm. In some embodiments, the sample preparation system 900 can inscribe an arc of 5 degrees to 30 degrees, and in some embodiments, between 15 degrees and 20 degrees. The liquid composition 914 may be agitated for at least 10 seconds, in some embodiments, at least 15 seconds, in some embodiments, at least 30 seconds, in some embodiments, at least 40 seconds, and in some embodiments, at least 60 seconds. In some embodiments, the liquid composition 914 can be agitated for at most 15 minutes, in some embodiments, at most 10 minutes, in some embodiments, at most 5 minutes, and in some embodiments, at most 3 minutes.

In some embodiments, the liquid composition 914 can be vortexed in a VX-2500 Multi-Tube Vortexer (VWR Scientific Products, West Chester, Pa.) at an agitation frequency of 200 to 5000 rpm, and in some embodiments, of 1000 to 3000 rpm for a selected duration of time. The vortex orbit can be linear, circular, elliptical, random, or a combination thereof. In some embodiments, the orbit is between 0.25 cm and 5 cm, and in some embodiments, between 1 cm and 3 cm.

As mentioned above, an array or plurality of sample preparation systems 100, 200, 300, 400, 500, 600, 700, 800 and/or 900 can be agitated simultaneously, by being placed on a plate, an arm or other device, and secured by gravity, clamping or other means for subsequent agitation. For example, in some embodiments, one to about fifty sample preparation systems 100, 200, 300, 400, 500, 600, 700, 800 and/or 900 are agitated simultaneously, and in some embodiments, about 10 to about 25 sample preparation systems 100, 200, 300, 400, 500, 600, 700, 800 and/or 900 are agitated simultaneously on a single agitation device or with multiple agitation devices.

In some embodiments, the liquid composition 914 can be agitated by the addition of a mechanical stirrer having a shaft and stirring blades, which may be inserted through the lid opening 954 (e.g., when no filter 934 is present), or alternatively, through any of the other possible apertures. Agitation of the liquid composition 914 may be further accomplished with steel ball bearings, magnetic stirring bars, blades, and other means to assist in breaking up and/or dispersing the loaded substrate 915 and/or the source 912 in the diluent 913 to release the analyte(s) of interest (if present) from the source 912. The agitation methods described above are included by way of example only and are not intended to be limiting. One of ordinary skill in the art will understand that other similar agitation methods can be employed.

The liquid composition 914 can be filtered using the filter 934 to form a filtrate 916 positioned within the filter 934 that includes the diluent 913 and any analyte(s) of interest (if present) in the diluent 913. All or a portion (e.g., a sample) of the filtrate 916 can be removed from the interior of the filter 934 for further processing (e.g., analysis).

In some embodiments, the level 965 of the liquid composition 914 is high enough that the filter 934 is positioned partially above and partially below the level 965 of the liquid composition 914. The sample preparation system 900 can be positioned upright, tipped, tilted or inverted to adjust the level 965 of the liquid composition 914 as necessary. In such embodiments, the interior of the filter 934 can be accessed via the lid opening 954, and a sample of the filtrate 916 can be removed via aspiration (e.g., by pipetting) from the interior of the filter 934. Alternatively, the filtrate 916 can be removed by decanting the filtrate 916 from the lid opening 954, and/or the liner 904 can be deformed and the filtrate 916 forced from the lid opening 954 by applying pressure to the liner 904 (e.g., to the base 926 of the liner 904 via the aperture 924 in the base 927 of the container 902).

In some embodiments, the level 965 of the liquid composition 914 is below the bottom of the filter 934, such that the filter 934 is positioned wholly above the level 965 of the liquid composition 914. In such embodiments, the sample preparation system 900 can be at least partially inverted to cause the liquid composition 914 to be filtered by the filter 934, such that the filtrate 916 is located within the filter 934. Pressure (i.e., positive or negative) can be applied to the liner 904 as described above to force the filtrate 916 into the interior of the filter 934, and/or from the lid opening 954. Alternatively, the filter 934 can be configured such that when the sample preparation system 900 is returned to an upright position after inversion, the filter 934 retains the filtrate 916 in its interior that can be removed by aspiration and/or decanting.

As described above, in some embodiments, such as the sample preparation system 200 illustrated in FIG. 4, the filter 234 can act as a retainer or holder for the loaded substrate 215. In such embodiments, a diluent 213 can be added to the first reservoir 220 of the container 202 (or the container 202 can be pre-filled with a pre-measured amount of diluent 213), and the loaded substrate 215 can be positioned within the filter 234. The lid 206 can be coupled to the container 202, and the sample preparation system 200 can be closed using a cover or similar closure device. The assembled and closed sample preparation system 200 can be agitated to allow the diluent 213 to flow into and out of the filter 234, such that the liquid composition 214 is located within the filter 234, and the filtrate 216 is located outside of the filter 234 and within the first reservoir 220 of the container 202.

As mentioned above, the filtrate 216 can be removed from any of a variety of sampling ports (e.g., the sampling port 232), and can be further filtered to removed additional particulates that may still be present in the filtrate 216. For example, the filtrate 216 can be further filtered by a filter 234' having a smaller pore size than that of the filter 234 coupled to the sidewall 229 of the container 202, such that a second filtrate 216' is formed within the filter 234'. The second filtrate 216', or a sample thereof, can be removed using any of the above-described techniques.

The above description of the use of the sample preparation system 900 is described by way of example only and is not intended to be limiting. Based on the above descriptions of the sample preparation method 10, and the various embodiments of the sample preparation system described above, one of skill in the art should understand the various ways in which the sample preparation system of the present disclosure can be used to prepare samples.

The embodiments described and exemplified above and illustrated in the figures are presented by way of example only and are not intended as a limitation upon the concepts and principles of the present invention. As such, it will be appreciated by one having ordinary skill in the art that various changes in the elements and their configuration and arrangement are possible without departing from the spirit and scope of the present invention. Various features and aspects of the invention are set forth in the following claims.

What is claimed is:

1. A system for preparing samples to test a surface for an analyte of interest, the system comprising:
    a freestanding container comprising a first reservoir;
    a deformable self-supporting receptacle dimensioned to be received in the first reservoir of the freestanding container and comprising a second reservoir, the freestanding container being more rigid than the deformable self-supporting receptacle, the freestanding container including a base comprising an aperture formed therein through which the deformable self-supporting receptacle can be accessed;
    a loaded substrate positioned in the second reservoir of the deformable self-supporting receptacle, the loaded substrate comprising a substrate and a source collected from the surface, the substrate comprising at least one of a sponge, a wipe, a towel, a cloth, a mop head, a swab, a film, a brush, and a combination thereof;
    a diluent positioned in the second reservoir of the deformable self-supporting receptacle in fluid communication with the loaded substrate; and
    a liquid composition positioned in the second reservoir, the liquid composition comprising the source and the diluent.

2. The system of claim 1, further comprising a lid coupled to at least one of the freestanding container and the deformable self-supporting receptacle.

3. The system of claim 1, wherein at least one of the source and the loaded substrate includes the diluent.

4. The system of claim 1, wherein the substrate comprises at least one of a polymer, a ceramic, a fabric, a paper, a woven thereof, a nonwoven thereof, and a combination thereof.

5. The system of claim 1, wherein the substrate comprises at least one of a metal-coated web, an adhesive-coated web, an electrostatically-charged web, a fibrous web, a foam, a film, a cellulosic material, and a combination thereof.

6. The system of claim 1, wherein the analyte of interest comprises at least one of *Salmonella* spp., *Acinetobacter* spp., *Vibrio* spp., *Listeria monocytogenes*, *Escherichia coli*, *Staphylococcus aureus*, *Clostridium perfringens*, *Campylo-*

*bacter jejuni, Pseudomonas aeruginosa, Bacillus anthracis, Bacillus cereus, Clostridium difficile*, methicillin-resistant *Staphylococcus aureus*, vancomycin-resistant *Enterococcus, Norovirus, Norwalk virus, Rotavirus, Adenovirus*, and a combination thereof.

7. The system of claim 1, wherein the analyte of interest comprises at least one of staphylococcal enterotoxin, *Bacillus diarrheal toxin, Clostridium difficile* toxin, aflatoxin, peanut allergen, egg allergen, and a combination thereof.

8. The system of claim 1, wherein the diluent includes at least one of a surfactant, a rheological agent, an antimicrobial neutralizer, a nutrient, a growth inhibitor, a pH buffering agent, an enzyme, an indicator molecule, sterile water, an organic solvent, and a combination thereof.

9. The system of claim 1, wherein the source collected from the surface is collected from an area of the surface of at least about 10 cm$^2$.

10. The system of claim 1, wherein the deformable self-supporting receptacle includes a sidewall, and wherein the sidewall includes a plurality of pleats or folds.

11. The system of claim 1, wherein the deformable self-supporting receptacle includes a sidewall, and wherein the sidewall includes at least one fold adapted to allow the sidewall to collapse at the at least one fold.

12. The system of claim 1, wherein the substrate is at least 100 cm$^2$.

13. A method for preparing samples to test a surface for an analyte of interest, the method comprising:
   providing a loaded substrate, the loaded substrate comprising a substrate and a source collected from the surface, the substrate comprising at least one of a sponge, a wipe, a towel, a cloth, a mop head, a swab, a film, a brush, and a combination thereof;
   providing a sample preparation system comprising:
      a deformable self-supporting receptacle dimensioned to be received in a freestanding container, the freestanding container being more rigid than the deformable self-supporting receptacle, the freestanding container including a base comprising an aperture formed therein through which the deformable self-supporting receptacle can be accessed, the deformable self-supporting receptacle comprising a reservoir;
   combining the loaded substrate and a diluent in the reservoir;
   agitating the loaded substrate and the diluent to form a liquid composition comprising the source and the diluent; and
   removing a sample from the sample preparation system by applying pressure to the deformable self-supporting receptacle.

14. The method of claim 13, wherein agitating includes at least one of manual shaking, mechanical shaking, sonicating, vortex stirring, manual stirring, mechanical stirring, manual beating, mechanical beating, blending, kneading, tumbling, and a combination thereof.

15. The method of claim 13, wherein applying pressure to the deformable self-supporting receptacle includes applying external pressure to the deformable self-supporting receptacle via the aperture in the freestanding container.

16. The method of claim 13, wherein the sample preparation system further includes a lid, wherein the loaded substrate is coupled to the lid, and wherein combining the loaded substrate and the diluent in the reservoir includes coupling the lid to at least one of the deformable self-supporting receptacle and the freestanding container.

17. A system for preparing samples to test a surface for an analyte of interest, the system comprising:
   a freestanding container comprising a first reservoir;
   a deformable self-supporting receptacle dimensioned to be received in the first reservoir of the freestanding container and comprising a second reservoir, the freestanding container being more rigid than the deformable self-supporting receptacle;
   a loaded substrate positioned in the second reservoir of the deformable self-supporting receptacle, the loaded substrate comprising a substrate and a source collected from the surface, wherein the substrate is at least 100 cm$^2$;
   a diluent positioned in the second reservoir of the deformable self-supporting receptacle in fluid communication with the loaded substrate; and
   a liquid composition positioned in the second reservoir, the liquid composition comprising the source and the diluent.

18. The system of claim 17, wherein the source collected from the surface is collected from an area of the surface of at least about 1 m$^2$.

19. The system of claim 17, wherein at least one of the source and the loaded substrate includes the diluent.

20. The system of claim 17, wherein the substrate comprises at least one of a sponge, a wipe, a towel, a cloth, a mop head, a swab, a brush, and a combination thereof.

* * * * *

UNITED STATES PATENT AND TRADEMARK OFFICE
CERTIFICATE OF CORRECTION

PATENT NO.        : 8,563,264 B2
APPLICATION NO.   : 12/743245
DATED             : October 22, 2013
INVENTOR(S)       : Kurt J. Halverson et al.

Page 1 of 1

It is certified that error appears in the above-identified patent and that said Letters Patent is hereby corrected as shown below:

Title Page, Item (75) Inventors:
Line 7, Delete "Husdon," and insert -- Hudson, --, therefor.

Title Page 2, Column 2, Item (56) Other Publications:
Line 1, Delete "Usefullness" and insert -- Usefulness --, therefor.
Line 11-12, Delete "Bactheriological" and insert -- Bacteriological --, therefor.

In the Specifications:

Column 7
Line 9, Delete "Micrococaceae," and insert -- Micrococcaceae, --, therefor.

Signed and Sealed this
Twenty-second Day of April, 2014

Michelle K. Lee
*Deputy Director of the United States Patent and Trademark Office*